(12) United States Patent
Sterner et al.

(10) Patent No.: US 8,802,654 B2
(45) Date of Patent: Aug. 12, 2014

(54) ANTIVIRAL COMPOUNDS

(75) Inventors: Olov Sterner, Malmö (SE); Ulf Ellervik, Löddeköpinge (SE); Karolina Aplander, Helsingborg (SE); Anders Carlsson, Stockholm (SE)

(73) Assignee: Adenovir Pharma AB, Helsingborg (SE)

(*) Notice: Subject to any disclaimer, the term of this patent is extended or adjusted under 35 U.S.C. 154(b) by 144 days.

(21) Appl. No.: 13/382,463

(22) PCT Filed: Jul. 5, 2010

(86) PCT No.: PCT/EP2010/059579
§ 371 (c)(1),
(2), (4) Date: Feb. 9, 2012

(87) PCT Pub. No.: WO2011/003876
PCT Pub. Date: Jan. 13, 2011

(65) Prior Publication Data
US 2012/0129795 A1 May 24, 2012

Related U.S. Application Data
(60) Provisional application No. 61/223,900, filed on Jul. 8, 2009.

(30) Foreign Application Priority Data
Jul. 7, 2009 (SE) .................................... 0950531

(51) Int. Cl.
*C07H 15/04* (2006.01)
*C07H 15/12* (2006.01)

(52) U.S. Cl.
USPC .......................................... 514/62; 536/17.9

(58) Field of Classification Search
None
See application file for complete search history.

(56) References Cited

FOREIGN PATENT DOCUMENTS

| | | | |
|---|---|---|---|
| EP | 0489162 A1 | | 6/1992 |
| EP | 0957107 A1 | | 11/1999 |
| JP | 6-80686 A | | 3/1994 |
| WO | WO 91/13079 A1 | | 9/1991 |
| WO | WO01/37846 | * | 5/2001 |
| WO | WO 01/37846 A1 | | 5/2001 |
| WO | WO 03/004672 A1 | | 1/2003 |

OTHER PUBLICATIONS

International Search Report for PCT/EP2010/059579, mailed on Nov. 17, 2010.
C. Guo et al., "Synthetic Sialylphosphatidylethanolamine derivatives bind to human influenza A viruses and inhibit viral infection", Glycoconjugate Journal, vol. 15, 1998, pp. 1099-1108, XP-000957949.
G. Glick et al., "Molecular Recognition of Bivalent Sialosides by Influenza Virus", Journal of Am. Chem. Soc., vol. 113, No. 12, 1991, pp. 4701-4703.
G. Wadell et al., "Adenoviruses", Manuel of Clinical Microbiology, 7th ed. ASM, Press, Washington, 1999, pp. 970-982.
G. Wadell et al., "Characterization of Candidate Adenovirus 37 by SDS-Polyacrylamide Gel Electrophoresis of Virion Polypeptides and DNA Restriction Site Mapping", Journal of Medical Virology, vol. 7, 1981, pp. 119-125.
H. Kaneko et al., "Epidemiological and virological features of epidemic keratoconjunctivitis due to new human adenovirus type 54 in Japan", British Journal of Ophthalmology, published online Jun. 8, 2010.
H. Kaneko et al., "Physicochemical Studies on the Phospholipid Bilayer Incorporated Sialoglycolipid", Chemical and pharmaceutical Bulletin, vol. 45, No. 6, 1997, pp. 951-956, XP-000693783.
H. Yamauchi et al., "Effects of sialic acid derivative on long circulation time and tumor concentration of liposomes", International Journal of Pharmaceutics, vol. 113, No. 2, 1995, pp. 141-148.
H. Yan et al., "Synthesis of mono- and di-sialophospholipids via the H-phosphonate approach 1", Canadian Journal of Chemistry, vol. 84, No. 4, 2006, pp. 540-545, XP-002608270.
J.C. de Jong et al., "Adenovirus 37: Indentification and Characterization of a Medically Important New Adenovirus Type of Subgroup D", Journal of Medical Virology, vol. 7, 1981, pp. 105-118.
K. Araki-Sasaki et al., "An SV-40-immortalized humancorneal epithelial cell lineand its characterization", Invest. Ophtahlmol., vol. 36, 1995, pp. 614-621.
M. Koketsu et al., "Synthesis of a Novel Sialic Acid Devivative (Sialylphospholipid) as an Antirotaviral Agent", Journal of Medicinal Chemistry, vol. 40, No. 21, 1997, pp. 3332-3335, XP-002608269.
M. Walsh et al., "Evidence of Molecular Evolution Driven by Recombination Events Influencing Tropism in a Novel Human Adenovirus that Causes Epidemic Keratoconjunctivitis", PLoS One, vol. 4, No. 6, pp. 1-14, Jun. 2009.
N. Arnberg et al., "Adenovirus type 37uses sialic acid as a cellular receptor", Journal of Virology, vol. 74, No. 1, 2000, pp. 42-48.
S. Johansson et al., "Multivalent HSA Conjugates of 3'-Sialyllactose are Potent Inhibitors of Adenoviral Cell Attachment and Infection", ChemBioChem, vol. 6, No. 2, 2005, pp. 358-364.

(Continued)

*Primary Examiner* — Traviss C. McIntosh, III
(74) *Attorney, Agent, or Firm* — Birch, Stewart, Kolasch & Birch, LLP

(57) ABSTRACT

Herein are disclosed novel compounds according to Formula (I) and aggregates comprising such compounds. These aggregates are useful to treat and prevent ocular infections caused by a virus, which virus binds to terminal sialic residues present on the cell surface of the cell to be infected by the virus.

(I)

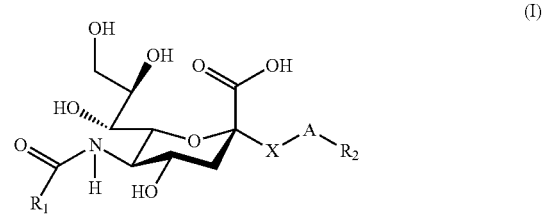

20 Claims, 3 Drawing Sheets

(56) References Cited

OTHER PUBLICATIONS

S. Johansson et al., "Multivalent sialic acid conjugates inhibit adenovirus type 37 from binding to and infecting human corneal epithelial cells", ScienceDirect, Antiviral Research, vol. 73, 2007, pp. 92-100.

W. Burmeister et al., "Crystal Struture of Species D Adenovirus Fiber Knobs and Their Sialic Acid Binding Sites", Journal of Virology, vol. 78, No. 12, 2004, pp. 7727-7736.

W. Lee et al., "Polyacrylamides Bearing Pendant•-Sialoside Group Strongly Inhibit Agglutination of Erythrocytes by Influentza A Virus: Multivalency and Steric Stabilization of Particulate Biological Systems", Journal of Med. Chem., vol. 37, No. 20, 1994, pp. 3419-3433.

X. Sun et al., "Synthesis of C-3-Modified Sialylglycosides as Selective Inhibitors of Influenza Hemagglutinin and Neuraminidase", European Journal of Organic Chemistry, vol. 14, No. 1, 2000, pp. 2643-2653, XP-002322783.

* cited by examiner

ANTIVIRAL COMPOUNDS

CROSS-REFERENCE TO RELATED APPLICATIONS

This application is the National Phase of PCT/EP2010/059579 filed on Jul. 5, 2010, which claims the benefit under 35 U.S.C. 119(e) of U.S. Provisional Application No. 61/223,900 filed Jul. 8, 2009, and claims priority under 35 U.S.C. 119(a) to Patent Application No. 0950531-4 filed in Sweden on Jul. 7, 2009, all of which are hereby expressly incorporated by reference into the present application.

FIELD OF THE INVENTION

The present invention relates to novel antiviral compounds, antiviral aggregates comprising such compounds, pharmaceutical compositions comprising such aggregates, and a method of treating or preventing epidemic keratoconjunctivitis and other ocular diseases caused by virus, which virus binds to terminal sialic residues present on the cell surface, by use of such compounds.

BACKGROUND

Epidemic keratoconjunctivitis (EKC) is a serious and contagious eye infection (conjunctiva and cornea) caused by the adenoviruses HAdV-8, HAdV-19, and HAdV-37 of speciesHAdV-D, and HAdV-4 of speciesE.

Furthermore, HAdV-53 of species D has also been reported to cause EKC (PLoS One, 2009, 4(6), 1-14, doi:10.1371/journal.pone.0005635.g001). In addition, a adenovirus denoted HAdV-22,37/H8 have been isolated from patients with EKC.

Recently, a virus denoted HAdV-54 has also been reported to cause EKC. (British Journal of Ophthalmology (2010) Hisatoshi Kaneko et al, "Epidemiological and virological features of epidemic keratoconjunctivitis due to new human adenovirus type 54 in Japan" published online Jun. 8, 2010, doi: 10.1136/bjo.2009.178772)

The symptoms of EKC are inflammation in the conjunctiva (conjunctivitis) and in the cornea (keratitis), pain, edema, diminished eye sight, tearing, sensitivity to light, feeling of a foreign body in the eye and development of pseudo membranes. During the acute phase of the disease (approximately two to three weeks), viruses are present and replicating. One of the eyes is normally infected first and it spreads to the other eye within two to three days. The infection in the first eye is normally more serious. In approximately 30% of patients' corneal opacities that result in deteriorating eye vision remains for weeks, months, or even years.

Since the disease is often epidemic in nature, it is called epidemic keratoconjunctivitis (EKC).

The patient is unable or is recommended by a doctor not to go to work or school due to the symptoms and the highly contagious nature of the disease. Approximately 45% of people in the patient's close surroundings, e.g., family members, become infected. The recurrence rate is 25% (within five years) after a first infection and 50% after a second.

EKC is transferred between individuals via physical contact, e.g. from eye to hand, from hand to a door knob, from door knob to another person's hand, and then to an uninfected eye. Viruses causing EKC can survive on e.g. door knobs, towels etc. for months. Adequate infection control measures must be followed in order to prevent and reduce epidemic outbreaks.

Treatment of the acute phase of the infection with topical steroids has been widely used. However, recent findings conclude that steroids may prolong the persistence in the cornea and frequent use may lead to long-lasting dry eye symptoms. The recommendation is that steroids should be avoided in both the acute and the chronic phase of the disease.

This highly contagious disease can be found all over the world, but is more common in heavily populated countries in Asia. Adenovirus conjunctivitis is particularly problematic in Japan where about one million cases of EKC is reported each year.

EKC occurs worldwide sporadically and epidemically and is endemic in East Asia, including Japan, Korea and Taiwan. It has gained recognition as a major health problem in these regions. The economic and social costs of this community epidemic are also high. Work places, public institutions, such as schools and children's day care centers', must be closed following the outbreak of an epidemic. Many work hours are lost every year as a consequence of the disease.

Although EKC normally heals up within 2 to 3 weeks, the costs to society in terms of both health care costs and loss of production because of its highly contagious nature are very substantial. The disease also has long-term implications for eyesight and recurrence.

The adenoviruses causing the EKC interact with their cellular receptors through fiber proteins that extend from the virus particle. Each particle has 12 homotrimeric fiber proteins, and thus, the receptor binding domain of the fiber (the knob) presents three separate binding sites.

The cellular receptor of HAdV-37 has been found to be a glycoconjugate carrying at least one terminal sialic acid moiety linked through an $\alpha 2,3$, glycosidic bond to the neighboring saccharide chain. Thus, the ability of adenoviruses HAdV-8, HAdV-19, HAdV-37, and presumably also other adenoviruses causing severe forms of EKC, such as HAdV-53, HAdV-54, and HAdV-22,37/H8, is strongly associated with their ability to bind to sialic acid on the cell surface. An antiviral drug based on sialic acid may therefore have the potential to block viral attachment. Accordingly, such a drug may possibly be used to treat patients suffering from EKC. Furthermore, it may possibly be used to prevent EKC.

WO 01/037846 discloses that adenoviral infections and in particular ocular adenoviral infections, e.g. kerato-conjunctivitis, may be treated or alleviated by the administration of a substance, interfering with the interaction between the virus and the sialic acid receptor, such as sialic acid, in a therapeutically effective amount.

Unfortunately the weak interactions between carbohydrates and proteins limit the use of carbohydrates as drugs. Attempts to overcome said limitations have been made (Johansson, S. M. C., et al Antiviral Research 73 (2007) 92-100) by using a glycoconjugate with several sialic acid derivatives linked to human serum albumin (SA-HSA).

However, such polyvalent glycoconjugates are for several reasons not suitable as pharmaceuticals.

The exact structure and composition of SA-HSA will vary between different molecules. Accordingly, SA-HSA represents a type of structure which is hard to structurally define. Furthermore, the composition of the SA-HSA derivatives will vary between different batches even if produced in the same manner. From a safety and a regulatory perspective this is a significant drawback.

In addition the use of a protein, i.e. HSA, which is derived from human plasma, is a major disadvantage. The origin of HSA makes it hard to produce larger amounts of a pharmaceutical based on HSA. Furthermore, contamination by infectious agents, such as viruses or prions, may not be excluded in HSA derived from human plasma.

Accordingly, a product based on HSA, is not suitable as a pharmaceutical product, and a polyvalent alternative would be highly desirable.

Currently, no clinically applicable specific antiviral therapy is available to shorten the course of the infection, to improve the distressful clinical symptoms, to stop viral replication, or to prevent the development of corneal opacities.

Accordingly, EKC is a disease where there is a lack of effective treatment and a large unmet medical need. A pharmaceutical that could be used for the treatment of EKC as well as for the prevention of its spread would be therefore highly desirable.

SUMMARY

The present invention seeks to mitigate, alleviate, circumvent or eliminate at least one, such as one or more, of the above-identified deficiencies.

Accordingly there is, according to one aspect of the invention, provided, a compound, which may be represented with the general formula (I)

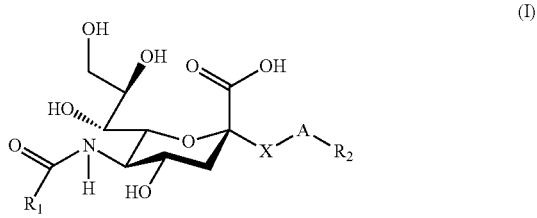

(I)

wherein R1 is a methyl or ethyl group; R2 is R3, R4 or R8; X is O, S, or NH; and "A" is a C3-7 alkanediyl if R2 is R3 and a C2-7 alkanediyl if R2 is R4 or R8, wherein "X" and R2 are connected to different carbon atoms of said alkanediyl and wherein said different carbon atoms are the carbon atoms in said alkanediyl being most spaced apart; R3 is selected from the group consisting of N(C0-3 alkyl)C(O)R5, OC(O)R5, C(O)N(C0-3 alkyl)R5 and C(O)OR5, wherein R5 is a straight carbon chain comprising 14 to 30 carbon atoms; said carbon chain is saturated or comprises one or more double and/or triple bond(s); furthermore, said carbon chain is unsubstituted or substituted with one or more C1-C5 alkyl groups; R4 is substituent according to formula (II), $$D(CH_2)_m(OCH_2CH_2)_n(CH_2)_pER_7 \quad (II)$$

wherein "D" is connected to "A" and selected from the group consisting of N(C0-3 alkyl)C(O), OC(O), C(O)N(C0-3 alkyl) and C(O)O; the integer "m" is 0 (zero) to 3; the integer "n" is 1 to 15; the integer "p" is 0 (zero) to 3; "E" is selected from the group consisting of N(C0-3 alkyl)C(O), OC(O), C(O)N(C0-3 alkyl) and C(O)O; and R7 is selected from the group consisting of R5, as defined above, and R6, wherein R6 is a substituent according to formula (III)

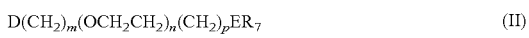

(III)

wherein each R5, independently, is as defined above, and the C2-5 alkyl is attached to "E"; and R8 is selected from the group consisting of N(C0-3 alkyl)C(O)R9, OC(O)R9, C(O)N(C0-3 alkyl)R9 and C(O)OR9, wherein R9 is a substituent according to formula (IV)

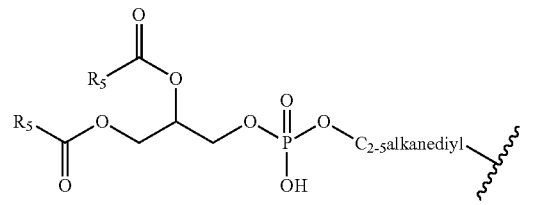

(IV)

wherein each R5, independently, is as defined above; as an acid in its non-charged protonated form, a pharmaceutically acceptable addition salt, a solvate, or a solvate of a salt thereof.

According to another aspect of the invention there is provided an aggregate comprising a plurality of a compound according to formula (I) and a plurality of an amphiphilic molecule separate from said compound and capable of forming bilayers in water.

According to another aspect of the invention there is provided a pharmaceutical composition comprising an aggregate, as disclosed above and at least one pharmaceutical acceptable excipient.

According to another aspect of the invention a compound according to formula (I), an aggregate, as disclosed above, or a pharmaceutical composition, as disclosed above, may be used in therapy.

According to another aspect of the invention a compound according to formula (I), an aggregate, as disclosed above, or an pharmaceutical composition, as disclosed above, may be used in the treatment and/or prevention of an ocular infection, such as epidemic keratoconjunctivitis, caused by a virus, which virus binds to terminal sialic residues present on the cell surface of the cell to be infected by said virus. Examples of such viruses include HAdV-8, HAdV-19, HAdV-37, HAdV-53, HAdV-54, and HAdV-22,37/H8.

Further, advantageous features of various embodiments of the invention are defined in the dependent claims and within the detailed description below.

DETAILED DESCRIPTION OF PREFERRED EMBODIMENTS

Figure 1:
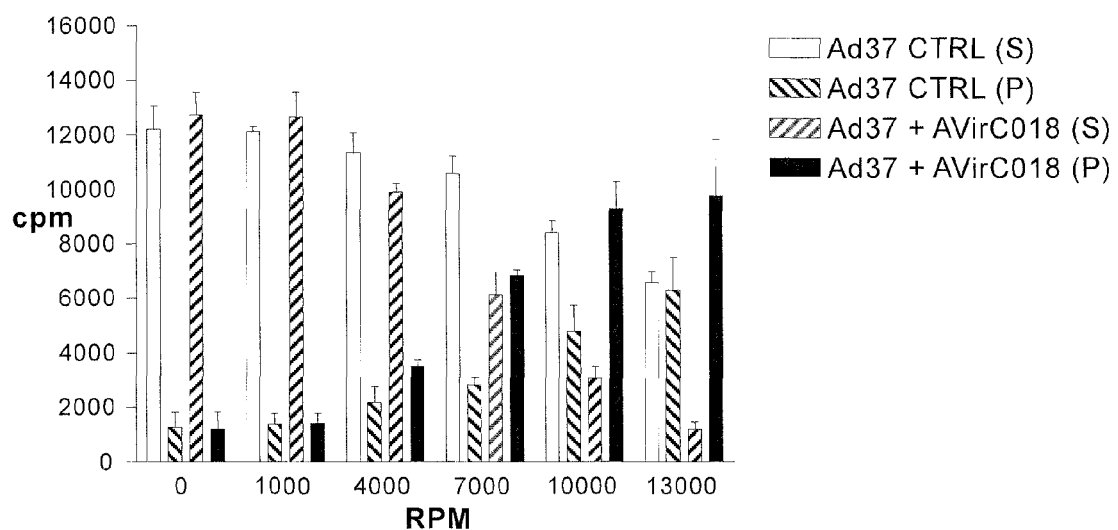
FIG. 1 depicts the ability of aggregates according to the present invention to cause aggregation of HAdV37.

The term "addition salt" is intended to mean salts formed by the addition of a pharmaceutical acceptable acid, such as organic or inorganic acids, or a pharmaceutical acceptable base. The organic acid may be, but is not limited to, acetic, propanoic, methanesulfonic, benzenesulfonic, lactic, malic, citric, tartaric, succinic or maleic acid. The inorganic acid may be, but is not limited to, hydrochloric, hydrobromic, sulfuric, nitric acid or phosphoric acid. The base may be, but is not limited to, ammonia and hydroxides of alkali or alkaline earth metals. The term "addition salt" also comprises the hydrates and solvent addition forms, such as hydrates and alcoholates.

As used herein, "alkyl" used alone or as a suffix or prefix, is intended to include both branched and straight chain saturated aliphatic hydrocarbon groups having a specified number of carbon atoms. For example "C1-6 alkyl" denotes alkyl having 1, 2, 3, 4, 5 or 6 carbon atoms.

As used herein, "alkanediyl", used alone or as a suffix or prefix, is intended to include both branched and straight chain saturated aliphatic hydrocarbon groups having a specified number of carbon atoms.

For example, "C1-6 alkanediyl" denotes alkanediyl having 1, 2, 3, 4, 5 or 6 carbon atoms.

As used herein, the groups linked by an alkanediyl-group, if not indicated, may be attached to any of the carbon atoms of the alkanediyl-group.

Examples of alkyl include, but are not limited to, methyl, ethyl, n-propyl, i-propyl, n-butyl, i-butyl, sec-butyl, t-butyl, pentyl, and hexyl.

Examples of alkanediyl include, but are not limited to, methylene, ethylene (etandiyl), propylene (propandiyl), and butylene (butandiyl).

Compounds

One embodiment of the invention relates to a compound according to formula (I)

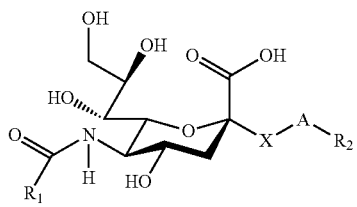

(I)

wherein R1 is a methyl or ethyl group; R2 is R3, R4, or R8; X is O, S, or NH; and "A" is a C3-7 alkanediyl if R2 is R3 and a C2-7 alkanediyl if R2 is R4 or R8; wherein "X" and R2 are connected to different carbon atoms of said alkanediyl and wherein said different carbon atoms are the carbon atoms in said alkanediyl being most spaced apart; R3 is selected from the group consisting of N(C0-3 alkyl)C(O)R5, OC(O)R5, C(O)N(C0-3 alkyl)R5 and C(O)OR5, wherein R5 is a straight carbon chain comprising 14 to 30 carbon atoms; said carbon chain is saturated or comprises one or more double and/or triple bond(s); furthermore, said carbon chain is unsubstituted or substituted with one or more C1-C5 alkyl groups; R4 is substituent according to formula (II), D(CH$_2$)$_m$(OCH$_2$CH$_2$)$_n$(CH$_2$)$_p$ER$_7$ (II)

wherein "D" is connected to "A" and selected from the group consisting of N(C0-3 alkyl)C(O), OC(O), C(O)N(C0-3 alkyl) and C(O)O; the integer "m" is 0 (zero) to 3; the integer "n" is 1 to 15; the integer "p" is 0 (zero) to 3; "E" is selected from the group consisting of N(C0-3 alkyl)C(O), OC(O), C(O)N(C0-3 alkyl) and C(O)O; and R7 is selected from the group consisting of R5, as defined above, and R6, wherein R6 is a substituent according to formula (III)

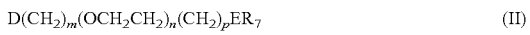

(III)

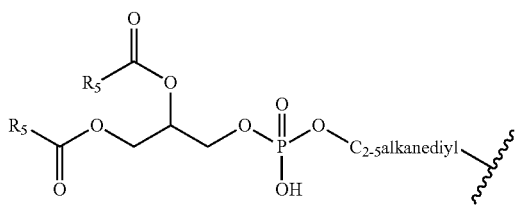

wherein each R5, independently, is as defined above, and the C2-5 alkyl is attached to E; and R8 is selected from the group consisting of N(C0-3 alkyl)C(O)R9, OC(O)R9, C(O)N(C0-3 alkyl)R9 and C(O)OR9, wherein R9 is a substituent according to formula (IV)

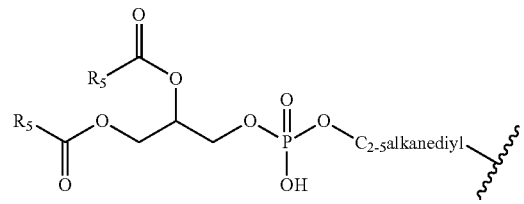

(IV)

wherein each R5, independently, is as defined above; as an acid in its non-charged protonated form, a pharmaceutically acceptable addition salt, a solvate, or a solvate of a salt thereof. Further, said compound may be present as a pure stereoisomer, or in a racemic, diastereomeric, scalemic or anomeric mixture comprising said compound. Preferably, said compound is present as a pure stereoisomer or as an anomeric mixture.

As disclosed above, R1 of formula (I) is a methyl or ethyl group. Preferably, R1 is a methyl group. Furthermore, "X" of formula (I) may, as disclosed above, be selected from O, S, or NH. Preferably, "X" is O. "A" in formula (I) is, as disclosed above, a C3-7 alkanediyl, if R2 is R3, or a C2-7 alkanediyl, if R2 is R4 or R8. Preferably, said C3-7 alkanediyl and said C2-7 alkanediyl are non-branched straight chain alkanediyls, such as being pentan-1,5-diyl.

One embodiment of the invention relates to a compound according to formula (I), wherein "A" is a non-branched, straight chain C3-5 alkanediyl, such as pentan-1,5-diyl, R1 is methyl, X is O and R5 is a unsubstituted straight carbon chain.

One embodiment of the invention relates to a compound according to formula (I), wherein R1 is methyl, "X" is O, R5 is a unsubstituted straight carbon chain, R2 is R4 or R8 and "A" is non-branched, straight chain C2-5 alkanediyl, such as etan-1,2-diyl or pentan-1,5-diyl.

As disclosed above, R2 of formula (I) is R3, R4 or R8. Preferably R2 is R4 or R8, and most preferably R2 is R4. However, R2 may also be R3.

As disclosed above, R5 of formula (I) is a straight carbon chain comprising 14 to 30 carbon atoms. The carbon chain may optionally comprise one or more double and/or triple bond(s). Furthermore, said carbon chain may optionally be substituted with one or more, such 1 to 3, C1-C5 alkyl groups, such as methyl groups. Preferably, R5 comprises 20 to 30 carbon atoms, such 24 to 26 carbon atoms. Although R5 may be substituted, it is preferred if R5 is unsubstituted.

According to one embodiment, R5 does comprise at least one double or triple bond. Preferably, R5 does comprise at least one triple bond and more preferably two conjugated triple bonds. Thus, R5 may for example be 9,11-tetracosadiynyl group.

According to one embodiment, R5 is straight carbon chain comprising 20 to 30 carbon atoms and two conjugated triple bonds, such as R5 being 9,11-tetracosadiynyl group.

As disclosed above, R4 is substituent according to formula (II). Although the integer "p" may be 0 (zero) to 3, it is preferred if "p" is 0 (zero). The integer "m", which may be 0 (zero) to 3, is preferably 2 or 3. Although the integer "n" may be 1 to 15, it is preferred for "n" to be 3 or more, such as 4 or 5 or more. Furthermore, although the integer "n" may up to 15, it is preferred for "n" to be 12 or less.

According to one embodiment, R2 is R4 and the integer "n" is 4 to 15. The presence of such a polyethyleneglycol linker seems to enhance the anti-viral activity, which is further discussed below, of an aggregate comprising a compound according to formula (I).

In compounds wherein "n" is 4 or more, it is preferred if R5 comprises 20 carbon atoms or more.

As disclosed above, "D" of formula (II) is selected from the group consisting of N(C0-3 alkyl)C(O), OC(O), C(O)N(C0-3 alkyl) and C(O)O. Preferably, "D" is selected from the group consisting of N(C0-1 alkyl)C(O) and C(O)N(C0-1 alkyl). Most preferably, "D" is NHC(O).

As disclosed above "E" is selected from the group consisting of N(C0-3 alkyl)C(O), OC(O), C(O)N(C0-3 alkyl) and C(O)O. Preferably, "E" is selected from the group consisting of N(C0-1 alkyl)C(O) and OC(O). If "E" is selected from the group consisting of N(C0-1 alkyl)C(O) and OC(O), then R5 is part of carboxylic acid residue. Most preferably, "E" is NHC(O).

Although R7 may be selected from R5 and R6, it is preferred for R7 to be R5.

If R2 is R4 and R7 is R6, then the C2-5 alkanediyl of R6 is preferably etan-1,2-diyl(ethylene) and "E" is preferably C(O)NH.

According to one embodiment, R2 is R4, "D" is NHC(O) or OC(O), the integer "m" is 2, the integer "p" is 0 (zero), "E" is NHC(O) or OC(O) and R7 is R5. In such an embodiment, it is preferred if R1 is methyl and if X is O. Furthermore, its preferred if "A" is a straight chain C2-C5 alkanediyl, such as etan-1,2-diyl or pentane-1,2-diyl. In addition, it is preferred for the integer "n" to be 3 or more in such an embodiment.

According to one embodiment, R2 is R4, "D" is C(O)NH or C(O)O, the integer "m" is 2, the integer "p" is 0 (zero), "E" is NHC(O) or OC(O), and R7 is R5. In such an embodiment, it is preferred if R1 is methyl and X is O. Furthermore, it is preferred that A is a straight chain C2-C5 alkanediyl, such as etan-1,2-diyl or pentane-1,2-diyl. In addition, it is preferred for the integer "n" to be 3 or more in such an embodiment.

Although, as disclosed above, it is preferred for R2 to be R4 or R8, one embodiment of the invention relates to a compound according to formula (I), wherein R2 is R3 and R3 is NHC(O)R5 or OC(O)R5. Preferably, R3 is NHC(O)R5 in such an embodiment.

According to one embodiment, a compound according to formula (I) may be selected from the group consisting of 6,19-diaza-10,13,16-trioxa-7,20-dioxo-tritetrakontanyl 5-acetamido-3,5-dideoxy-D-glycero-α-D-galacto-2-nonylopyranosylonic acid, 6,25-diaza-10,13,16,19,22-pentaoxa-7,26-dioxo-nonatetrakontanyl 5-acetamido-3,5-dideoxy-D-glycero-α-D-galacto-2-nonylopyranosylonic acid, 6,46-diaza-10,13,16,19,22,25,28,31,34,37,40,43,46-dodekaoxa-7,47-dioxo-tetrahexakontanyl 5-acetamido-3,5-dideoxy-D-glycero-α-D-galacto-2-nonylopyranosylonic acid, 6,19-diaza-10,13,16-trioxa-7,20-dioxo-29,31-tetratetrakonta-diynyl 5-acetamido-3,5-dideoxy-D-glycero-α-D-galacto-2-nonylopyranosylonic acid 6,25-diaza-10,13,16,19,22-pentaoxa-7,26-dioxo-35,37-pentakontadiynyl 5-acetamido-3,5-dideoxy-D-glycero-α-D-galacto-2-nonylopyranosylonic acid and 6,46-diaza-10,13,16,19,22,25,28,31,34,37,40,43,46-dodekaoxa-7,47-dioxo-56,58-henheptakonta-diynyl 5-acetamido-3,5-dideoxy-D-glycero-α-D-galacto-2-nonylopyranosylonic acid. A compound according to formula (I) may be selected from the group consisting of 6,19-diaza-10,13,16-trioxa-7,20-dioxo-29,31-tetratetrakonta-diynyl 5-acetamido-3,5-dideoxy-D-glycero-α-D-galacto-2-nonylopyranosylonic acid, 6,25-diaza-10,13,16,19,22-pentaoxa-7,26-dioxo-35,37-pentakontadiynyl 5-acetamido-3,5-dideoxy-D-glycero-α-D-galacto-2-nonylopyranosylonic acid and 6,46-diaza-10,13,16,19,22,25,28,31,34,37,40,43,46-dodekaoxa-7,47-dioxo-56,58-henheptakonta-diynyl 5-acetamido-3,5-dideoxy-D-glycero-α-D-galacto-2-nonylopyranosylonic acid.

As disclosed above some embodiments of the present invention relates to a compound according to formula (I), as an acid in its non-charged protonated form, a pharmaceutically acceptable addition salt, such as an acid in its deprotonated form, solvate, or solvate of a salt thereof. Further, the compound according to formula (I) may be present as a pure stereoisomer or as an anomeric mixture.

If present in an anomeric mixture, it is preferred if the α-anomer prevails. Accordingly, its is preferred if 75% or more, such as more than 90%, 95%, 99% or even more than 99.9% of a compound is present as the α-anomer.

Aggregates

As the cellular receptor part of the cell membrane, which adenovirus causing EKC uses to adhere to the cell, has terminal sialic acid residues, a plurality of a compound, as described herein, were incorporated into an amphiphilic aggregate comprising a plurality of an amphiphilic molecule capable of forming bilayers in water and separate from said compound. Such aggregates were found to inhibit the binding of HAdV-37 to human corneal cells more effective than the compound in monovalent form.

An aggregate comprising amphiphilic molecule, capable of forming bilayers in water, may be present as a bilayer with a lipophilic interior.

Without being bound to any theory, it seems that such an aggregate may be characterized as polyvalent aggregate with respect to the number of sialic acid residues in a single aggregate available for binding to adenovirus. Hence, such aggregates may be used to treat and/or prevent EKC more effectively than a corresponding sialic acid residue or sialic acid it self.

Thus, such an aggregate may overcome several of the disadvantages with the use of SA-HSA. In particular, the constituents of the aggregate are well defined molecules and the aggregate will be free from any infectious agents.

Accordingly, one embodiment of the present invention relates to an aggregate comprising a plurality of a compound as disclosed herein and a plurality of a molecule separate from said compound. Such a molecule may be an amphiphilic molecule capable of forming bilayers in water. The aggregate may comprise a bilayer formed by said molecule. As the aggregate comprises amphiphilic molecule capable of forming bilayers in water, it may resemble a cellular membrane. Therefore, compounds having a major lipophilic part, such as the compounds as disclosed herein, may be inserted into the aggregate.

When inserted into such an aggregate in an aqueous solution, the sialic acid residue of a compound, as disclosed herein, will be presented to the surrounding aqueous media. The lipophilic part of the compounds comprising R5 of formula (I) will be buried in the aggregate.

Said aggregate may comprise at least 40 mol % of an amphiphilic molecule capable of forming bilayers in water. Preferably, it comprises 50 mol % or more, such as 65, 75 or even 85 mol % or more, of said molecule.

Similarly, the content of said amphiphilic molecule may also be determined on weight basis. Accordingly, an aggregate, as disclosed herein, may comprise 40 wt % or more of an amphiphilic molecule capable of forming bilayers in water. Preferably, it comprises 50 wt % or more, such as 65, 75 or even 85 wt % or more, of said amphiphilic molecule.

The aggregates as disclosed herein may comprise 50 mol % or less of a compound as disclosed herein. The content of said compound may be 25, 15, 10 or 5 mol % or less.

A too high content of said compound may impart the stability of the aggregate. Furthermore a too high content may place the discrete compounds presenting sialic acid residues to the surrounding aqueous media to close to each other. On the contrary, a too low content may lead to an unsatisfactory binding to the virus. Accordingly, the content of said compound, according to one embodiment, may be 0.1 to 25 mol %, such as 5 to 15 mol %. According to another embodiment the content is about 10 mol %.

Similarly, the content of said compound, according to one embodiment, may be 0.1 to 25 wt %, such as 1 to 15 wt % or 5 to 15 wt %. According to another embodiment the content is about 10 wt %.

Typically, an amphiphilic molecule capable of forming a bilayer in water comprises at least one, such as one or two, lipophilic carbon chain(s). Said chain(s) may be saturated. Furthermore, said chain(s) may be unsaturated and thus comprising one or several double and/or triple bonds. Although such carbon chain(s) may be branched, it is preferred if said carbon chain(s) is/are linear. The carbon chain(s) typically constitutes the major part of the lipophilic part of said amphiphilic molecule. It may comprise more than 12 carbon atoms. According to one embodiment, the carbon chain comprises 16 carbon atoms or more, such as 20 carbon atoms or more.

Although any molecule capable of forming a bilayer in water may be used, it may be advantageous to use a molecule comprising a linear carbon chain, wherein said carbon chain comprises at least one triple bond, such as two conjugated triple bonds.

According to one embodiment said molecule capable of forming a bilayer in water may be selected from molecules comprising a 9,11-tetracosadiynyl group. One example of such a molecule is 10,12-pentacosadiynoic acid.

If the constituents of the aggregate comprises conjugated triple bonds, such as 10,12-pentacosadiynoic acid does, the constituents of the aggregate may be polymerized by treatment with UV-radiation. One embodiment of the invention thus relates to such an aggregate, wherein said aggregate have been treated with UV-radiation to cause polymerization.

A compound according to formula (I), present in an aggregate as disclosed herein, and comprising conjugated triple bonds, such as R5 of formula (I) being 9,11-tetracosadiynyl, may be part of such a polymeric network formed be treatment with UV-radiation.

The degree of polymerization in such aggregates may, according to one embodiment, be at least 50% or more, such as 60, 70 or even 80%, or more. In this context, degree of polymerization is intended to mean the percentage of the triple bonds which have became part of the polymer network polymerized.

According to another embodiment, aggregates which may be polymerized, such as by treatment with UV-radiation, have been treated with care in order to avoid polymerization, such as by avoiding exposure to UV-radiation. According, to one embodiment 10% or less, such as 5, 1 or even 0.1% or less, of the constitutes in the aggregate, which may be polymerized, have been polymerized.

In one embodiment, R5 in formula (I) is selected from a moiety also present in the amphiphilic molecule being part of the aggregate. For example, if R5 is 9,11-tetracosadiynyl, then said molecule may be 10,12-pentacosadiynoic acid. Furthermore, if said molecule is phospholipid being a diester of glycerol, then R5 may be selected from the carbon chain in one of the fatty acid residues in said ester.

Typically, an amphiphilic molecule capable of forming a bilayer in water comprises a hydrophilic moiety. Examples of such hydrophilic moieties comprise a carboxy group, a phosphate group, esters of phosphates, such as choline, serine and glycerol esters, sulphate group, amines, saccharides, such as mono saccharides and disaccharides, and hydroxy groups.

As disclosed above, the aggregates should comprise amphiphilic molecules capable of forming bilayers in water. Such molecules may be selected from carboxylic acids comprising more than 12 carbon atoms, phosphoglycerides, such as phosphatidylcholines, phosphatidylserines, and phosphatidylethanolamines, and sphingomyelines.

According to one embodiment, the amphiphilic molecules capable of forming bilayers in water may be selected from amphiphilic molecules having a transition temperature of more than 40° C., such as more then 50 or 60° C. As well known to the one skilled in the art, transition temperature in this context means the temperature where the transition from an ordered phase (also known as gel phase) to a disordered liquid crystalline phase of a bilayer, formed by the amphiphilic molecule in water, takes places.

Aggregates of amphiphilic molecules forming bilayers in water may be present as liposomes, i.e. one or more spherical bilayer encompassing a part of the aqueous solution in which the liposomes were formed. Such aggregates may also be present as bilayers in form of sheets. Furthermore, amphiphilic molecules may also form micelles in water. However, micelles do not comprise any bilayer.

According to one embodiment, the aggregate, as disclosed herein, is a sheet comprising one or more bilayers, such as 1 to 5.

In contrast to a liposome, both sides of the bilayer in a sheet with a single bilayer will be facing the surrounding aqueous media. Thereby all the sialic residues of the compounds in the sheet will be available for binding of virus.

Furthermore, it seems that aggregates in form of sheets comprising one or several bilayers give rise to a more effective inhibition of the binding of HAdV-37 to human corneal cells.

The size of such sheets may vary depending on the preparation procedure.

According to one embodiment the mean width of the sheets may be up to several micrometers, such as up to 10 to 100 μm.

The size of the aggregates, which may be present as sheets, may be reduced by sonication. Such sonication may take place prior to formulating the aggregate into a medicament. According to one embodiment the mean width of such sheets with a reduced size may be 1 μm or less.

A reduced aggregate size is preferred from colloidal stability point of view, as smaller aggregates tend agglomerate and sediment to a lesser extent than larger would do. A reduction in size may be accomplished by subjecting the aggregates to, inter alia, ultrasonication, extrusion, or high-pressure homogenization, such as by use of a Emulsifix C50 High-pressure homogenizer (F160). Preferably, theses procedures are performed above the transition temperature of the amphiphilic molecules constituting the bilayers.

The transition temperature of the amphiphilic molecules forming the aggregate may not only influence the fluidity of the bilayer, but also the actual form of the aggregate. Amphiphilic molecules having a transition temperature above the ambient temperature will be more prone to form sheets, while amphiphilic molecules having a transition temperature below the ambient temperature will be more prone to form liposomes.

Accordingly, the amphiphilic molecule to be part of the aggregate as disclosed herein may, according to one embodiment, be selected from amphiphilic molecules having a transition temperature above room temperature, such as a having transition temperature of 40, 50 or even 60° C. or higher.

The transition temperature of the amphiphilic molecules is not only affected by the length of the carbon chain, but also by presence of double and/or triple bonds. Double bonds are known to lower the transition temperature, as the bond disrupts the otherwise regular periodic structure and thereby negatively affects the Van der Waals interactions. Less is known regarding the effect of triple bond and specifically the effect of conjugated triple bonds.

Without being bound to any theory it may be that the good activity obtained with aggregates comprising 10,12-pentacosadiynoic acid, at least partly, is due to the fact the such aggregates seems to be present as sheets rather than liposomes. It may be that the conjugated triple bonds favor such a form.

According to one embodiment, aggregates, as disclosed herein, may further comprise additional components. As one example components affecting the fluidity and the stability of the aggregate may be used. One example of such component is cholesterol. Typically such other components will be present in an amount equal or less to the amount of the amphiphilic molecule. According to one embodiment, the content of such as additional component, such as cholesterol, may be 1:1 to 1:10 (additional component, such as cholesterol: amphiphilic molecule).

Formation of Aggregates

Aggregates as disclosed herein may be obtained by procedures familiar to the one skilled in the art. Such procedures include sonication and/or extrusion of aqueous solutions or suspensions comprising a compound, as disclosed herein, and an amphiphilic molecule, as disclosed herein.

Furthermore, examples of such procedures include dissolution of dried films in aqueous solutions.

According to one embodiment, an aggregate as disclosed herein, may be obtained by:
  dissolving a compound, as disclosed herein, and an amphiphilic molecule, as disclosed herein, in an organic solvent, such as chloroform, dichloromethane, methanol, ethanol, hydrocarbons, such as hexane and heptane, or mixtures thereof;
  applying said solution to a surface;
  evaporating the organic solvent; and
  dispersing the resulting film in an aqueous solution; optionally said solution may then be sonicated. Such a sonication step is preferably performed at a temperature above room temperature, such as at or above 40° C.

Formulation

Another embodiment of the invention relates to a pharmaceutical composition, e.g. a medicament for treatment and/or prevention of EKC, comprising an aggregate, which aggregate, as has been described herein, comprises a compound according to formula (I). Such a pharmaceutical composition may further comprise pharmaceutically acceptable excipients, such as carriers, diluents, and/or stabilizers.

"Pharmaceutically acceptable" means an excipient that, at the dosage and concentration employed, does not cause any unwanted effects in the patients to whom it is administered. Such pharmaceutically acceptable excipients are well-known in the art.

According to one embodiment, such a pharmaceutical composition as disclosed herein is a pharmaceutical composition suitable to be administered to the eye.

Without limitation typical example pharmaceutical compositions suitable for administration to the eye comprise eye drops, ointments, sprays, dressings and gels.

According to one embodiment a pharmaceutical composition as disclosed herein comprises 0.001 to 10 mg/ml, such as 0.01 to 5 mg/ml or 0.01 to 1 mg/ml, of an aggregate, which aggregate, as has been described herein above, comprises a substance according to formula (I).

Further, a pharmaceutical composition as disclosed herein may comprise 0.001 to 10 mM, such as 0.01 to 1 mM of a substance according to formula (I).

According to one embodiment a pharmaceutical composition as disclosed herein may be an aqueous composition. Such an aqueous composition may have a water content of 90 wt % water or more, such as 90 to 99.9, 95 to 99 or 95 to 98 wt % water.

Furthermore an aqueous composition may comprise an agent to provide an isotonic solution. Accordingly, an aqueous composition may comprise an agent selected from the group consisting of sodium chloride, glycerol, polyethyleneglycol, sacharides, such as monosacharides, eg. glucose and mannitol, and disaccharides, e.g. sucrose.

According to one embodiment a pharmaceutical composition as disclosed herein is an aqueous composition comprising an electrolyte, such as sodium chloride. Preferably said content should be close to the iso-osmotic concentration, such as about 0.9 wt %.

According to one embodiment a pharmaceutical composition as disclosed herein is an aqueous composition comprising glycerol. The content of glycerol may be 2 to 3 wt %, such as 2.3 to 2.3 or 2.5 to 2.7 wt %. Preferably said content should be close to the iso-osmotic concentration, such as about 2.6 wt %.

According to one embodiment an aqueous pharmaceutical composition as disclosed herein has a pH of about 6.5 to 8. Preferably said pH should be close to physiological pH, such as about 7.2 to 7.8.

As compounds according to formula (I) comprises a carboxylic acid moiety, said pharmaceutical composition may comprise a pharmaceutical acceptable acid and/or base to adjust the pH to the desired level. Similarly, the pharmaceutical composition may also comprise buffering species, such as $HCO_3^-/CO_3^{2-}$ or $H_2PO_4^-/HPO_4^{2-}$.

According to another embodiment, the pH of the pharmaceutical composition is not adjusted after the aggregate as disclosed herein have been added. Accordingly, such an embodiment relates to an aqueous pharmaceutical composition as disclosed herein, which has a pH of about 5 to 7. A composition with an acidic pH, i.e. below 7, may have the advantage of being less susceptible to the growth of microorganisms.

According to one embodiment a pharmaceutical composition as disclosed herein may comprise a preservative. Examples of such preservatives benzalkonium chloride, benzoic acid, butylated hydroxyanisol, parabens, such as butyl paraben, propyl paraben, ethyl paraben, methyl paraben and mixtures thereof, phenoxyethanol, phenylethyl alcohol or sorbic acid. A pharmaceutical composition comprising a preservative may be more suitable for storage.

Further, a pharmaceutical composition as disclosed herein may be sterilized, such as by heat sterilization or by sterile filtration.

According to one embodiment a pharmaceutical composition as disclosed herein may also comprise other pharmaceutically acceptable excipients, such as preservatives, antioxidants, additional isotonicity agents, colouring agents and the like.

In embodiments relating to aqueous suspensions, a pharmaceutical composition, as disclosed herein, may comprise suspending and stabilising agents, such as non-ionic surfactants, hydrophilic polymers and the like.

According to one embodiment, a pharmaceutical composition as disclosed herein may comprise a thickening agent. Thickening agents may be employed in order to create a thickened solution, gel, syrup, cream, or ointment. In order to form a thickened solution or gel, a hydrogel-forming material may be employed. Such a hydrogel-forming material may be selected from the group consisting of synthetic polymers, semi-synthetic polymers and natural gums.

According to one embodiment, the pharmaceutical composition, as disclosed herein, is a thickened aqueous solution. The typical viscosity of such a solution may be in the range of 1 to 100 mPas, more typically 5 to 50 or 10 to 25 mPas.

Examples of synthetic polymers include polyvinylalcohol, polyvinylpyrolidone, polyacrylic acid, polyethylene glycol, poloxamer block copolymers.

Examples of semi-synthetic polymers include cellulose ethers, such as carboxymethylcellulose, hydroxyethylcellulose, hydroxypropylcellulose, methylcellulose, hydroxypropylmethylcellulose and ethylhydroxyethylcellulose.

Examples of natural gums include acacia, alginate, carragenan, chitosan, pectin, starch, xanthan gum.

A thickened solution or gel may be rendered mucoadhesive by employment of materials such as hyaluronic acid and derivatives thereof, cross-linked polyacrylic acids of the carbomer and polycarbophil types, and polymers that readily form gels, which are known to adhere strongly to mucous membranes.

According to one embodiment a pharmaceutical composition as disclosed herein may comprise a block copolymer of the poloxamer type. It is advantageous to use the block copolymer of the poloxamer type, such as polymers comprising polyethylene glycol and polypropylene glycol blocks, as certain poloxamers dispersed in water are thermoreversible Examples of thermoreversible poloxamers are poloxamer 188 and poloxamer 407.

Thermoreversible poloxamers dispersed in water have a low viscosity but exhibit a marked viscosity increase at elevated temperatures, resulting in a gel formation at body temperature. Thereby the contact time of a pharmaceutical formulation administered to the relatively warm cornea may be prolonged. Accordingly, one embodiment of the invention relates to a pharmaceutical composition, as disclosed herein, which is thermoreversible.

According to one embodiment a pharmaceutical composition as disclosed herein may comprise an additional anti-viral compound. Examples of such compounds include N-chlorotaurin and Povidone-iodine (PVP-I).

N-chlorotaurine (Cl—HN—CH2-CH2-SO3H) is an endogenous antimicrobial agent. It is a mild active chlorine compound produced by granulocytes and monocytes during the oxidative burst. Because of its unspecific reaction mechanism, i.e. oxidation of amino groups, thio and aromatic compounds, it has broad-spectrum microbicidal activity similar to antiseptics. The sodium salt solution of N-chlorotaurine (Cl—HN—CH2-CH2-SO3Na) has been shown to kill in vitro bacteria and fungi. In addition, a virucidal effect has been demonstrated. Povidone-iodine is a stable chemical complex of polyvinylpyrrolidone (povidone, PVP) and elemental iodine.

According to one embodiment a pharmaceutical composition as disclosed herein may comprise an additional anti-viral compound, wherein said anti-viral compound is a compound useful to topically treat infections caused by herpes. Examples of such compounds include the guanosine analogues aciclovir, valaciclovir, penciclovir, and famciclovir, and foscarnet (sodium phosphoneformate hexahydrate).

According to one embodiment a pharmaceutical composition as disclosed herein may comprise a local anesthetic. As EKC may be a very painful disease, it may be advantageous to include a local anesthetic to provide pain relief. Furthermore, such pain relief may have the advantage of encouraging the patient to continue the treatment although the administration it self may be painful. In addition, use of local anesthetic with a rapid onset, may make it possible for the patient to actually open the eye in order to allow further administration of the composition directly to the cornea. Examples of useful local anesthetics include, lidocaine, prilocalne, and ropivacaine.

Therapy

According to another embodiment, a compound, an aggregate or a pharmaceutical composition, as disclosed herein may be used in therapy.

Treatment of Ocular Infections

As already disclosed above, the aggregate as disclosed herein was found to inhibit the binding of HAdV-37 to human corneal cells.

Accordingly, one embodiment of the invention relates a compound, an aggregate or a pharmaceutical composition, as disclosed herein, for use in the treatment and/or prevention of an ocular infection caused by a virus, which virus binds to terminal sialic residues present on the cell surface of the cell to be infected by said virus.

Similarly, one embodiment of the invention relates to use of a compound, an aggregate or a pharmaceutical composition, as disclosed herein, for the manufacture of a medicament for use in the treatment and/or prevention of an ocular infection caused by a virus, which virus binds to terminal sialic residues present on the cell surface of the cell to be infected by said virus.

According to one embodiment such a virus may be selected from the group consisting of HAdV-8, HAdV-19, HAdV-37, HAdV-53, HAdV-54 and HAdV-22,37/H8. Such a virus may also be selected from HAdV-8, HAdV-19 and HAdV-37, such as being HAdV-37.

According to one embodiment the ocular infection to be treated and/or prevented may be epidemic keratoconjunctivitis (EKC).

According to one embodiment the ocular infection treated and/or prevented may be acute hemorrhagic conjunctivitis. Acute hemorrhagic conjunctivitis is caused by viruses, such as Coxsackievirus-A 24 variant (CVA24v) and enterovirus type 70 (EV70).

Another embodiment relates to a method of prevention and/or treatment of an ocular infection caused by a virus, which virus binds to terminal sialic residues present on the cell surface of the cell to be infected by said virus, such as EKC, comprising administering to a mammal, including man, in need of such prevention and/or treatment, a therapeutically effective amount of compound or aggregate as disclosed herein or a pharmaceutical composition comprising a therapeutically effective amount of a compound as disclosed herein. Preferably, said compound, aggregate or pharmaceutical composition is administered to the eye in such a method.

A pharmaceutical composition according to embodiments herein may be administered to a patient in a pharmaceutically effective dose. By "pharmaceutically effective dose" is meant a dose that is sufficient to produce the desired effects in relation to the condition for which it is administered. The exact dose may be dependent on the activity of the compound, manner of administration, nature and severity of the disorder and/or disease and the general conditions, such as age and body weight of the patient.

According to one embodiment, a pharmaceutical composition as disclosed herein is to be administered one or several times per day. Typically, such a pharmaceutical composition will be administered three times a day.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

According to one embodiment treatment does also encompass pre-treatment, i.e. prophylactic treatment.

General Remarks

Although the present invention has been described above with reference to specific illustrative embodiments, it is not intended to be limited to the specific form set forth herein. Any combination of the above mentioned embodiments should be appreciated as being within the scope of the invention. Rather, the invention is limited only by the accompanying claims and other embodiments than the specific above are equally possible within the scope of these appended claims.

In the claims, the term "comprises/comprising" does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality.

EXPERIMENTAL

Compounds

Compounds A-K (see scheme 1) were synthesized using a block synthesis. Thus sialic acid 1 (Johansson, S. M. C.; Nilsson, E. C.; Elofsson, M.; Ahlskog, N.; Kihlberg, J.; Arnberg, N. Antiviral Res. 2007, 73, 92-100), coupled with an Fmoc-protected aminopentanol, was deprotected using piperidine in DMF. The crude product was coupled, using EDC.HCl, with either an Fmoc-protected polyethylene glycol linker (PEG 2, 4 or 11) to get compounds 2-4, or with PDA (10,12-pentacosadiynic acid) or hexadecanoic acid to get compound 14 and 15 respectively. Compounds 2-4 were deprotected using piperidine in DMF. The crude compounds were then coupled, using EDC.HCl, with stearic acid (to get compounds 5-7), with tetracosanoic acid (to get compounds 8-10), or with 10,12-pentacosadiynic acid (to get compounds 11-13). Compounds 5-15 were then deprotected by treatment of NaOMe (0.05 M in MeOH) for 1 h followed by the addition of 5 equiv. NaOH for another 18 h. The final compounds (A-K) were purified by column chromatography on $SiO_2$ using $CH_2Cl_2$:MeOH:$H_2O$ systems. The block synthesis facilitates the synthesis of new compounds by simple variation of linkers (e.g. linker length, linker type, bond type) and acids.

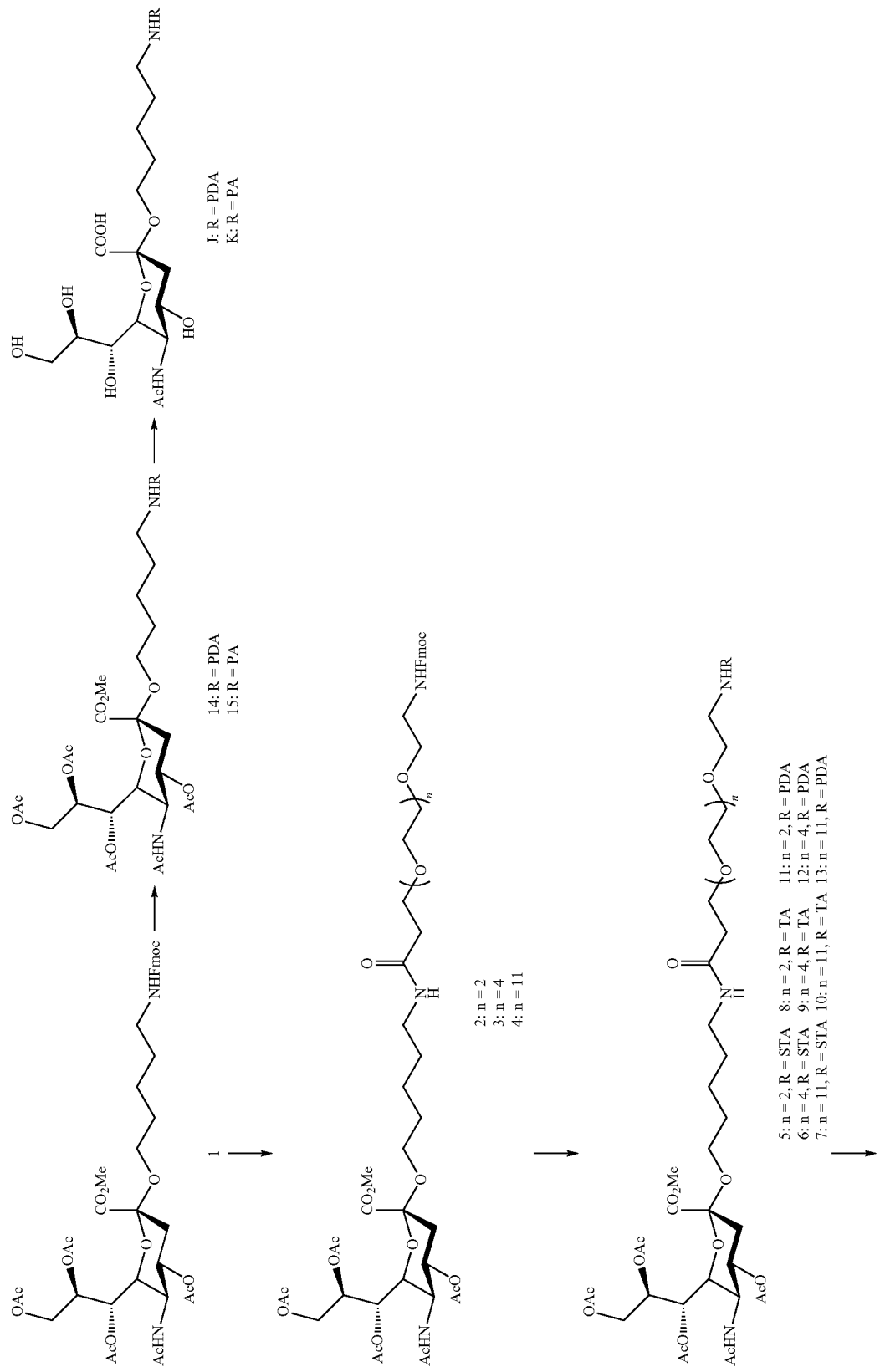

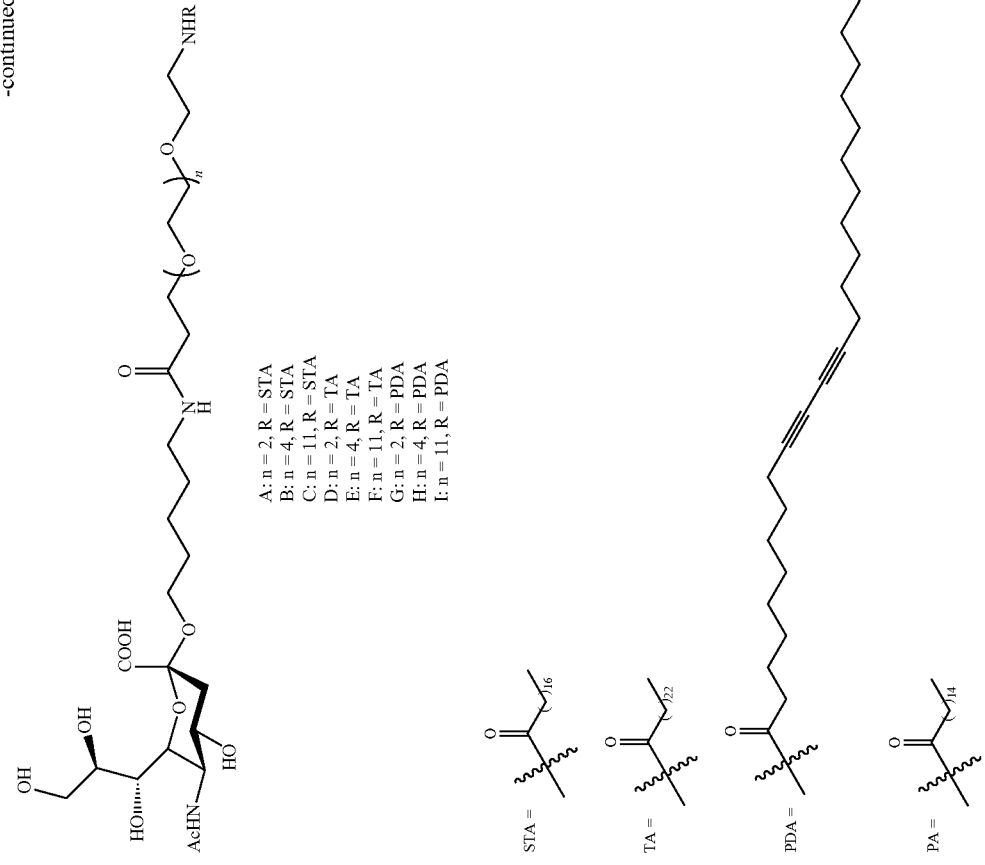

Experimental details for compounds A to K is disclosed below.

In generally;
i. Operations were carried out at ambient temperature, i.e. in the range 17 to 25° C. unless otherwise stated;
ii. Evaporations were carried out by rotary evaporation in vacuo;
iii. Column chromatography (by the flash procedure) was performed using standard glass-columns on silica gel (35-70 nm, 60 Å);
iv. Yields, where present, are not necessarily the maximum attainable;
v. In general, the structures of the end-products were confirmed by nuclear magnetic resonance (NMR) and/or mass spectral (MS) techniques; mass spectral data were obtained using a Micromass Q-T of (ESI); NMR chemical shift values were measured on the delta scale [proton magnetic resonance spectra were determined using a Bruker DRX 400 spectrometer operating at a field strength of 400 MHz]; the following abbreviations have been used: s, singlet; d, doublet; t, triplet; m, multiplet;
vi. Intermediates were not necessarily fully purified but their structures and purity were assessed by thin layer chromatographic and/or NMR analysis;
vii. The following abbreviations have been used:

| | |
|---|---|
| aq | aqueous |
| C | Celsius |
| d | doublet |
| DCM | dichloromethane |
| CDCl$_3$ | deuterated chloroform |
| DIPEA | N,N-diisopropylethylamine |
| DMF | N,N-dimethylformamide |
| DMSO | dimethylsulphoxide |
| EDC*HCl | N-Ethyl-N'-(3-dimethylaminopropyl)carbodiimide hydrochloride |
| ESI | electrosprayionization |
| EtOAc | ethylacetate |
| h | hour(s) |
| HRMS | high resolution mass spectra |
| H$_2$O | water |
| m | multiplet |
| MeOD | deuterated methanol |
| MeOH | methanol |
| MgSO$_4$ | magnesium sulfate |
| mg | milligram |
| MHz | megahertz |
| mL | milliliter |
| mmol | millimole |
| NaOH | sodium hydroxide |
| NaOMe | sodium methoxide |
| NMR | nuclear magnetic resonance |
| s | singlet |
| t | triplet |
| μL | microliter |

Compound 2

6,19-diaza-22-(9H-fluoren-9-yl)-10,13,16,21-tetraoxa-7,20-dioxo-dokosanyl methyl(5-acetamido-4,7,8,9-tetra-O-acetyl-3,5-dideoxy-D-glycero-α-D-galacto-2-nonylopyranosyl)onate 1 (150.9 mg, 0.189 mmol) was dissolved in dry DMF (5 mL) and then piperidine (706 pt, 7.14 mmol) was added to the solution. The reaction mixture was stirred for 2 h after which the solvent and remaining piperidine were evaporated under reduced pressure to give a crude intermediate. This crude intermediate (36.3 mg, 0.063 mmol) and Fmoc-NH-(PEG)2-COOH were dissolved in DCM (1 mL) and the solution was cooled to 0° C. EDC.HCl (18.2 mg, 0.095 mmol) was added to the solution. The reaction mixture was stirred for 18 h. The crude was subjected to flash column chromatography (DCM/MeOH 25:1) to give the title compound (45.0 mg, 71%).

$^1$H NMR (400 MHZ, CDCl$_3$) δ 1.28-1.57 (m), 1.87 (s, 3H), 1.90-1.96 (m), 2.01 (s, 3H), 2.02 (s, 3H), 2.13 (s, 3H), 2.13 (s, 3H), 2.42 (t, 2H), 2.53-2.58 (m, 1H), 3.17-3.27 (m, 3H), 3.38-3.40 (m), 3.55-3.62 (m), 3.68-3.78 (m), 4.02-4.10 (m, 3H) 4.21 (t, 1H), 4.29-4.33 (m, 1H), 4.40 (d, 2H), 4.79-4.86 (m, 1H), 5.19-5.22 (m, 1H), 5.29-5.32 (m, 1H), 5.37-5.44 (m, 2H), 6.37 (t, 1H), 7.28-7.32 (m, 2H), 7.39 (t, 2H), 7.60 (d, 2H), 7.76 (d, 2H).

HRMS calcd. for $C_{49}H_{67}N_3O_{19}$ (M+Na)$^+$ 1024.4266, found 1024.4921.

Compound 3

6,25-diaza-28-(9H-fluoren-9-yl)-10,13,16,19,22,28-hexaoxa-7,26-dioxo-oktaeikosanyl methyl(5-acetamido-4,7,8,9-tetra-O-acetyl-3,5-dideoxy-D-glycero-α-D-galacto-2-nonylopyranosyl)onate The following compound was synthesized analogously to Compound 2, using Fmoc-NH-(PEG)$_4$-COOH instead of Fmoc-NH-(PEG)$_2$-COOH.

Yield 83.4 mg (61%).

$^1$H NMR (400 MHZ, CDCl$_3$) δ 1.27-1.57 (m), 1.86-2.04 (m), 2.13 (s, 6H), 2.43 (t, 2H), 2.53-2.58 (m, 1H), 3.17-3.24 (m, 3H), 3.36-3.40 (m), 3.55-3.62 (m), 3.68-3.77 (m), 4.02-4.11 (m, 3H), 4.21 (t, 1H), 4.29-4.32 (m, 1H), 4.39 (d, 2H), 4.79-4.85 (m, 1H), 5.23-5.25 (m, 1H), 5.29-5.32 (m, 1H), 5.36-5.40 (m, 1H), 5.48 (t, 1H), 6.47 (t, 1H), 7.28-7.32 (m, 2H), 7.37-7.41 (m, 2H), 7.60 (d, 2H), 7.75 (d, 2H).

HRMS calcd. for $C_{53}H_{75}N_3O_{21}$ (M+Na)$^+$ 1112.4791, found 1112.5548.

Compound 4

6,46-diaza-49-(9H-fluoren-9-yl)-10,13,16,19,22,25,28,31,34,37,40,43,48-tridekaoxa-7,47-dioxo-nonatetrakontanyl methyl(5-acetamido-4,7,8,9-tetra-O-acetyl-3,5-dideoxy-D-glycero-α-D-galacto-2-nonylopyranosyl)onate The following compound was synthesized analogously to Compound 2, using Fmoc-NH-(PEG)11-COOH instead of Fmoc-NH-(PEG)$_2$-COOH.

Yield 45.8 mg (60%).

$^1$H NMR (400 MHZ, CDCl$_3$) δ 1.23-1.57 (m), 1.86 (s, 3H), 1.88-1.98 (m), 2.01 (s, 3H), 2.02 (s, 3H), 2.12 (s, 6H), 2.43 (t, 2H), 2.53-2.57 (m, 1H), 3.16-3.27 (m, 3H), 3.37-3.43 (m, 2H), 3.54-3.62 (m), 3.69-3.75 (m), 3.75-3.77 (m), 4.01-4.10 (m), 4.20 (t, 1H), 4.28-4.32 (m, 1H), 4.34-4.39 (m, 2H), 4.78-4.85 (m, 1H), 5.24-5.31 (m, 2H), 5.35-5.39 (m, 1H), 5.43 (t, 1H), 6.50 (t, 1H), 7.27-7.31 (m, 2H), 7.36-7.40 (m, 2H), 7.58-7.63 (m, 2H), 7.74 (d, 2H).

HRMS calcd. for $C_{67}H_{103}N_3O_{28}$ (M+Na)$^+$ 1420.6626, found 1420.7222.

Compound 5

6,19-diaza-10,13,16-trioxa-7,20-dioxo-heptatrikontanyl methyl(5-acetamido-4,7,8,9-tetra-O-acetyl-3,5-dideoxy-D-glycero-α-D-galacto-2-nonylopyranosyl)onate 2 (43.3 mg, 0.043 mmol) was dissolved in DMF (2 mL) and then piperidine (162 μL, 1.63 mmol) was added. The reaction mixture was stirred for 2.5 h. The solvent was evaporated to give crude intermediate. This crude intermediate was split into 2 equally batches. The crude intermediate from one of the batches was dissolved in DCM (1 mL) and then stearic acid (9.1 mg, 0.032 mmol) was added to the solution and the reaction was cooled to 0° C. EDC.HCl (6.1 mg, 0.032 mmol) was added to the solution. The reaction mixture was stirred for 16 h. The reaction mixture was washed with water (2×5 mL), dried over MgSO$_4$, filtered and concentrated under reduced pressure. The crude was subjected to flash column chromatography (DCM/MeOH 25:1→20:1) to give the title compound (6.3 mg, 28%).

$^1$H NMR (400 MHZ, CDCl$_3$) δ 0.87 (t, 3H), 1.23-1.31 (m), 1.32-1.63 (m), 1.87 (s, 3H), 1.92-1.96 (m), 2.02 (s, 3H), 2.03 (s, 3H), 2.14-2.18 (m), 2.45 (t, 2H), 2.54-2.58 (m, 1H), 3.20-3.24 (m, 3H), 3.43-3.46 (m, 2H), 3.53-3.56 (m, 2H), 3.59-3.64 (m), 3.71-3.77 (m), 3.79 (s, 3H), 4.02-4.11 (m), 4.30-4.34 (m, 1H), 4.79-4.86 (m, 1H), 5.20-5.22 (m, 1H), 5.29-5.32 (m, 1H), 5.36-5.41 (m, 1H), 6.13 (t, 1H), 6.42 (t, 1H).

HRMS calcd. for C$_{52}$H$_{91}$N$_3$O$_{18}$ (M+Na)$^+$ 1068.6195, found 1068.6290.

Compound 6

6,25-diaza-10,13,16,19,22-pentaoxa-7,26-dioxo-tritetrakontanyl methyl(5-acetamido-4,7,8,9-tetra-O-acetyl-3,5-dideoxy-D-glycero-α-D-galacto-2-nonylopyranosyl)onate The following compound was synthesized analogously to Compound 5, using 3 instead of 2.

Yield 14.2 mg (52%).

$^1$H NMR (400 MHZ, CDCl$_3$) δ 0.88 (t), 1.25-1.42 (m), 1.46-1.67 (m), 1.79-1.83 (m), 1.88 (s, 3H), 1.91-1.97 (m), 2.03, (s, 3H), 2.04 (s, 3H), 2.10-2.19 (m), 2.44-2.47 (t, 2H), 2.54-2.60 (m), 3.18-3.33 (m), 3.42-3.46 (m, 2H), 3.54-3.56 (m, 2H), 3.61-3.65 (m), 3.71-3.77 (m), 3.79 (s, 3H), 4.02-4.11 (m, 3H), 4.30-4.33 (m, 1H), 4.80-4.87 (m, 1H), 5.15-5.17 (m, 1H), 5.30-5.33 (m, 1H), 5.37-5.41 (m, 1H), 6.18 (t, 1H), 6.51 (t, 1H).

HRMS calcd. for C$_{56}$H$_{99}$N$_3$O$_{20}$ (M+Na)$^+$ 1156.6720, found 1156.7217.

Compound 7

6,46-diaza-10,13,16,19,22,25,28,31,34,37,40,43,46-dodekaoxa-7,47-dioxo-heptakontanyl methyl(5-acetamido-4,7,8,9-tetra-O-acetyl-3,5-dideoxy-D-glycero-α-D-galacto-2-nonylopyranosyl)onate The following compound was synthesized analogously to Compound 5, using 4 instead of 2.

Yield 6.0 mg (42%).

$^1$H NMR (400 MHZ, CDCl$_3$) δ 0.88 (t, 3H), 1.25-1.42 (m), 1.46-1.63 (m), 1.88 (s, 3H), 1.90-2.00 (m), 2.03 (s, 3H), 2.04 (s, 3H), 2.10-2.18 (m), 2.45 (t, 2H), 2.54-2.59 (m), 3.18-3.33 (m), 3.40-3.46 (m, 2H), 3.54-3.56 (m, 2H), 3.61-3.65 (m), 3.71-3.79 (m), 4.02-4.11 (m), 4.29-4.36 (m, 1H), 4.80-4.87 (m, 1H), 5.14-5.17 (m, 1H), 5.30-5.32 (m, 1H), 5.37-5.41 (m, 1H), 6.18 (t, 1H), 6.50 (t, 1H),

HRMS calcd. for C$_{70}$H$_{127}$N$_3$O$_{27}$ (M+Na)$^+$ 1464.8555, found 1464.8711.

Compound 8

6,19-diaza-10,13,16-trioxa-7,20-dioxo-tritetrakontanyl methyl(5-acetamido-4,7,8,9-tetra-O-acetyl-3,5-dideoxy-D-glycero-α-D-galacto-2-nonylopyranosyl)onate The following compound was synthesized analogously to Compound 5, using tetracosanoic acid instead of stearic acid.

Yield 15.9 mg (65%).

$^1$H NMR (400 MHZ, CDCl$_3$) δ 0.85-0.89 (m), 1.15-1.41 (m), 1.46-1.63 (m), 1.88-1.89 (m), 1.90-1.97 (m), 2.02 (s, 3H), 2.03 (s, 3H), 2.10-2.18 (m), 2.38-2.46 (m), 2.54-2.58 (m), 3.19-3.32 (m), 3.42-3.48 (m, 2H), 3.53-3.56 (m, 2H), 3.60-3.63 (m), 3.71-3.79 (m), 4.03-4.11 (m, 3H), 4.30-4.34 (m, 1H), 4.80-4.86 (m, 1H), 5.19-5.21 (m, 1H), 5.30-5.32 (m, 1H), 5.37-5.41 (m, 1H), 6.14 (t, 1H), 6.42 (t, 1H).

HRMS calcd. for C$_{58}$H$_{103}$N$_3$O$_{18}$ (M+Na)$^+$ 1152.7134, found 1152.7108.

Compound 9

6,25-diaza-10,13,16,19,22-pentaoxa-7,26-dioxo-nonatetrakontanyl methyl(5-acetamido-4,7,8,9-tetra-O-acetyl-3,5-dideoxy-D-glycero-α-D-galacto-2-nonylopyranosyl)onate The following compound was synthesized analogously to Compound 5, using 3 and tetracosanoic acid instead of 2 and stearic acid.

Yield 18.3 mg (63%).

$^1$H NMR (400 MHZ, CDCl$_3$) δ 0.87 (t, 3H), 1.24-1.40 (m), 1.46-1.62 (m), 1.87 (s, 3H), 1.90-1.96 (m), 2.02 (s, 3H), 2.03 (s, 3H), 2.10-2.18 (m), 2.43-2.46 (t, 2H), 2.54-2.59 (m), 3.17-3.30 (m), 3.41-3.45 (m, 2H), 3.53-3.56 (m, 2H), 3.60-3.64 (m), 3.70-3.76 (m), 3.78 (s, 3H), 4.02-4.11 (m), 4.29-4.33 (m, 1H), 4.79-4.86 (m, 1H), 5.22-5.24 (m, 1H), 5.29-5.32 (m, 1H), 5.36-5.40 (m, 1H), 6.15 (t, 1H), 6.51 (t, 1H),

HRMS calcd. for C$_{62}$H$_{111}$N$_3$O$_{20}$ (M+H)$^+$ 1218.7839, found 1218.7875.

Compound 10

6,46-diaza-10,13,16,19,22,25,28,31,34,37,40,43,46-dodekaoxa-7,47-dioxo-tetrahexakontanyl methyl(5-acetamido-4,7,8,9-tetra-β-acetyl-3,5-dideoxy-D-glycero-α-D-galacto-2-nonylopyranosyl)onate The following compound was synthesized analogously to Compound 5, using 4 and tetracosanoic acid instead of 2 and stearic acid.

Yield 6.2 mg (41%).

$^1$H NMR (400 MHZ, CDCl$_3$) δ 0.86-0.89 (m), 1.25-1.44 (m), 1.46-1.63 (m), 1.88 (s, 3H), 1.90-1.99 (m), 2.02 (s, 3H), 2.04 (s, 3H), 2.10-2.18 (m), 2.41-2.47 (m), 2.54-2.58 (m, 2H), 3.18-3.33 (m), 3.42-3.48 (m), 3.54-3.56 (m), 3.61-3.65 (m), 3.71-3.79 (m), 4.02-4.11 (m), 4.29-4.35 (m, 1H), 4.80-4.87 (m, 1H), 5.16-5.18 (m, 1H), 5.30-5.32 (m, 1H), 5.37-5.41 (m, 1H), 6.20 (t, 1H), 6.51 (t, 1H).

HRMS calcd. for C$_{76}$H$_{139}$N$_3$O$_{27}$ (M+Na)$^+$ 1548.9494, found 1548.9514.

Compound 11

6,19-diaza-10,13,16-trioxa-7,20-dioxo-29,31-tetratetrakonta-diynyl methyl(5-acetamido-4,7,8,9-tetra-O-acetyl-3,5-dideoxy-D-glycero-α-D-galacto-2-nonylopyranosyl)onate The following compound was synthesized analogously to Compound 5, using 10,12-pentacosadiynoic acid instead of stearic acid.

Yield 36.3 mg (73%).

$^1$H NMR (400 MHZ, CDCl$_3$) δ 0.86 (t, 3H), 1.23-1.41 (m), 1.42-1.61 (m), 1.86 (s, 3H), 1.89-1.97 (m), 2.01 (s, 3H), 2.02 (s, 3H), 2.08-2.18 (m), 2.20-2.23 (m), 2.43 (t, 2H), 2.53-2.59 (m, 1H), 3.18-3.31 (m), 3.4-3.44 (m, 2H), 3.52-3.55 (m, 2H), 3.59-3.62 (m), 3.69-3.75 (m), 3.77 (s, 3H), 4.01-4.10 (m), 4.28-4.32 (m, 1H), 4.78-4.85 (m, 1H), 5.28-5.39 (m, 3H), 6.11 (t, 1H), 6.43 (t, 1H).

HRMS calcd. for $C_{59}H_{97}N_3O_{18}$ (M+Na)$^+$ 1158.6665, found 1158.6655.

Compound 12

6,25-diaza-10,13,16,19,22-pentaoxa-7,26-dioxo-35,37-pentakontadiynyl methyl(5-acetamido-4,7,8,9-tetra-O-acetyl-3,5-dideoxy-D-glycero-α-D-galacto-2-nonylopyranosyl)onate The following compound was synthesized analogously to Compound 5, using 3 and 10,12-pentacosadiynoic acid instead of 2 and stearic acid.

Yield 21.9 mg (62%).

$^1$H NMR (400 MHZ, CDCl$_3$) δ 0.86 (t, 3H), 1.24-1.39 (m), 1.45-1.62 (m), 1.86 (s, 3H), 1.92-1.95 (m), 2.01 (s, 3H), 2.02 (s, 3H), 2.10-2.17 (m), 2.20-2.24 (m), 2.45 (t, 2H), 2.53-2.59 (m), 3.17-3.31 (m), 3.41-3.45 (m, 2H), 3.53-3.55 (m, 2H), 3.61-3.64 (m), 3.70-3.76 (m), 3.78 (s, 3H), 4.01-4.10 (m), 4.28-4.35 (m, 1H), 4.78-4.85 (m, 1H), 5.26-5.31 (m, 2H), 5.35-5.40 (m, 1H), 6.19 (t, 1H), 6.52 (t, 1H).

HRMS calcd. for $C_{63}H_{105}N_3O_{20}$ (M+Na)$^+$ 1246.7189, found 1246.7118.

Compound 13

6,46-diaza-10,13,16,19,22,25,28,31,34,37,40,43,46-dodekaoxa-7,47-dioxo-56,58-henheptakonta-diynyl methyl(5-acetamido-4,7,8,9-tetra-O-acetyl-3,5-dideoxy-D-glycero-α-D-galacto-2-nonylopyranosyl)onate The following compound was synthesized analogously to Compound 5, using 4 and 10,12-pentacosadiynoic acid instead of 2 and stearic acid.

Yield 25.2 mg (50%).

$^1$H NMR (400 MHZ, CDCl$_3$) δ 0.87 (t, 3H), 1.24-1.41 (m), 1.46-1.62 (m), 1.87 (s, 3H), 1.90-2.02 (m), 2.03 (s, 3H), 2.05 (s, 3H), 2.13-2.18 (m), 2.21-2.24 (m), 2.46 (t, 2H), 2.54-2.58 (m, 1H), 3.17-3.26 (m), 3.42-3.49 (m), 3.54-3.56 (m), 3.62-3.65 (m), 3.70-3.75 (m), 3.79 (s, 3H), 4.02-4.11 (m), 4.29-4.32 (m, 1H), 4.79-4.86 (m, 1H), 5.17-5.20 (m, 1H), 5.29-5.32 (m, 1H), 5.36-5.40 (m, 1H), 6.17 (s, 1H), 6.58 (s, 1H).

HRMS calcd. for $C_{77}H_{133}N_3O_{27}$ (M+Na)$^+$ 1554.9024, found 1554.9325.

Compound 14

6-aza-7-oxo-16,18-hentriakonta-diynyl methyl(5-acetamido-4,7,8,9-tetra-O-acetyl-3,5-dideoxy-D-glycero-α-D-galacto-2-nonylopyranosyl)onate 1 (121.9 mg, 0.153 mmol) was dissolved in DMF (5 mL) and then piperidine was added. The reaction mixture was stirred under a nitrogen atmosphere for 2 h. The solvent was evaporated to give crude intermediate. This crude intermediate was split into 2 equally batches. The crude intermediate from 1 of the batches was dissolved in DCM (1 mL) and then 10,12-pentacosadiynoic acid (37.1 mg, 0.099 mmol) was added to the solution and the reaction was cooled to 0° C. EDC.HCl (14.6 mg, 0.076 mmol) was added to the solution. The reaction mixture was stirred for 20 h. The reaction mixture was diluted with DCM and washed with water (3×5 mL), dried over MgSO$_4$, filtered and concentrated under reduced pressure. The crude was subjected to flash column chromatography (DCM/MeOH 25:1) to give the title compound (47.8 mg, 67%). Contaminated with 10,12-pentacosadiynoic acid according to NMR.

$^1$H NMR (400 MHZ, CDCl$_3$) δ 0.86 (t), 1.23-1.35 (m), 1.45-1.58 (m), 1.86 (s, 3H), 1.90-1.93 (m), 2.01 (s, 3H), 2.02 (s, 3H), 2.11-2.15 (m), 2.22 (t), 2.30 (t, 1H), 2.52-2.58 (m, 1H), 3.18-3.28 (m), 3.70-3.73 (m, 1H), 3.77 (s, 3H), 4.00-4.08 (m), 4.31-4.34 (m, 1H), 4.78-4.85 (m, 1H), 5.28-5.30 (m, 1H), 5.33-5.38 (m, 2H), 5.85 (t, 1H).

HRMS calcd. for $C_{50}H_{81}N_2O_{14}$ (M+H)$^+$ 933.5688, found 933.5718.

Compound 15

6-aza-7-oxo-dokosanyl methyl(5-acetamido-4,7,8,9-tetra-O-acetyl-3,5-dideoxy-D-glycero-α-D-galacto-2-nonylopyranosyl)onate The following compound was synthesized analogously to Compound 14, using 1 and hexadecanoic acid instead for 10,12-pentacosadiynoic acid.

Yield 37 mg (48%).

$^1$H NMR (400 MHZ, CDCl$_3$) δ 0.87 (t, 3H), 1.20-1.30 (m), 1.32-1.65 (m), 1.86 (s, 3H), 1.94 (t, 1H), 2.00-2.05 (m), 2.10-2.16 (m), 2.55 (dd, 1H), 3.15-3.30 (m), 3.72 (dt, 1H), 3.79 (s, 3H), 4.00-4.10 (m), 4.33 (dd, 1H), 4.79-4.87 (m), 5.15-5.20 (m), 5.30 (dd, 1H), 5.39 (ddd, 1H), 5.79 (bt, 1H).

Compound A 6,19-diaza-10,13,16-trioxa-7,20-dioxo-heptatrikontanyl 5-acetamido-3,5-dideoxy-D-glycero-α-D-galacto-2-nonylopyranosylonic acid 5 (6.0 mg, 0.006 mmol) was dissolved in NaOMe (600 μL, 0.05 M, in MeOH). The reaction was stirred for 2 h and then NaOH (30 μL, 1 M, in water) was added to the reaction mixture. The reaction mixture was stirred for 24 h and was then quenched with Duolite C436 until neutral pH was reached. The reaction mixture was filtered, rinsed with MeOH and concentrated under reduced pressure. The crude was subjected to flash column chromatography (DCM/MeOH/H$_2$O 80:15:5) to give the title compound in quantitative yield.

¹H NMR (400 MHZ, MeOD) δ 0.90 (t, 3H), 1.29 (m), 1.36-1.42 (m), 1.48-1.60 (m), 1.89 (m) 2.01 (s, 3H), 2.20 (t, 2H), 2.43-2.46 (m, 2H), 2.81-2.85 (m, 1H), 3.17 (t, 2H), 3.35-3.37 (m), 3.45-3.89 (m).
HRMS calcd. for $C_{43}H_{81}N_3O_{14}$ (M+Na)⁺ 886.5616, found 886.5621.

Compound B 6,25-diaza-10,13,16,19,22-pentaoxa-7,26-dioxo-tritetrakontanyl 5-acetamido-3,5-dideoxy-D-glycero-α-D-galacto-2-nonylopyranosylonic acid The following compound was synthesized analogously to Compound A, using 6 instead of 5.
Yield 3.1 mg (27%).
¹H NMR (400 MHZ, MeOD) δ 0.90 (t, 3H), 1.29-1.42 (m), 1.48-1.62 (m), 2.00 (s, 3H), 2.19 (t, 2H), 2.45 (t, 2H), 2.81-2.85 (m, 1H), 3.18 (t, 2H), 3.35-3.38 (m), 3.45-3.89 (m).
HRMS calcd. for $C_{47}H_{89}N_3O_{16}$ (M+Na)⁺ 951.6243, found.

Compound C 6,46-diaza-10,13,16,19,22,25,28,31,34,37,40,43,46-dodekaoxa-7,47-dioxo-heptakontanyl 5-acetamido-3,5-dideoxy-D-glycero-D-galacto-2-nonylopyranosylonic acid The following compound was synthesized analogously to Compound A, using 7 instead of 5.
Yield quantitative.
¹H NMR (400 MHZ, MeOD) δ 0.90 (t, 3H), 1.29-1.42 (m), 1.48-1.60 (m), 2.01 (s, 3H), 2.19 (t, 2H), 2.45 (t, 2H), 2.81-2.85 (m, 1H), 3.18 (t, 2H), 3.33-3.37 (m), 3.45-3.89 (m).
HRMS calcd. for $C_{61}H_{117}N_3O_{23}$ (M+Na)⁺ 1282.7976, found 1282.8201.

Compound D 6,19-diaza-10,13,16-trioxa-7,20-dioxo-tritetrakontanyl 5-acetamido-3,5-dideoxy-D-glycero-α-D-galacto-2-nonylopyranosylonic acid The following compound was synthesized analogously to Compound A, using 8 instead of 5.
Yield quantitative.
¹H NMR (400 MHZ, MeOD) δ 0.90 (t), 1.29-1.42 (m), 1.48-1.60 (m), 2.01 (s, 3H), 2.19 (t, 2H), 2.45 (t, 2H), 2.81-2.85 (m, 1H), 3.17 (t, 2H), 3.35-3.37 (m), 3.45-3.89 (m).
HRMS calcd. for $C_{49}H_{93}N_3O_{14}$ (M+Na)⁺ 970.6555, found 970.6328.

Compound E 6,25-diaza-10,13,16,19,22-pentaoxa-7,26-dioxo-nonatetrakontanyl 5-acetamido-3,5-dideoxy-D-glycero-α-D-galacto-2-nonylopyranosylonic acid The following compound was synthesized analogously to Compound A, using 9 instead of 5.
Yield 14.8 mg (95%).
¹H NMR (400 MHZ, MeOD) δ 0.90 (t), 1.29-1.60 (m), 2.01 (s, 3H), 2.19 (t, 2H), 2.45 (t, 2H), 2.81-2.84 (m, 1H), 3.12-3.19 (m), 3.35-3.37 (m), 3.47-3.87 (m).

HRMS calcd. for $C_{53}H_{101}N_3O_{16}$ (M+Na)⁺ 1058.7080, found 1058.6575.

Compound F 6,46-diaza-10,13,16,19,22,25,28,31,34,37,40,43,46-dodekaoxa-7,47-dioxo-tetrahexakontanyl 5-acetamido-3,5-dideoxy-D-glycero-α-D-galacto-2-nonylopyranosylonic acid The following compound was synthesized analogously to Compound A, using 10 instead of 5.
Yield quantitative.
¹H NMR (400 MHZ, MeOD) δ 0.90 (t), 1.29-1.40 (m), 1.49-1.59 (m), 2.00-2.01 (s, 3H), 2.13-2.21 (m), 2.45 (t, 2H), 2.81-2.85 (m, 1H), 3.12-3.19 (m), 3.35-3.37 (m), 3.45-3.88 (m).
HRMS calcd. for $C_{67}H_{129}N_3O_{23}$ (M+Na)⁺ 1366.8915, found 1388.9717.

Compound G 6,19-diaza-10,13,16-trioxa-7,20-dioxo-29,31-tetratetrakonta-diynyl 5-acetamido-3,5-dideoxy-D-glycero-α-D-galacto-2-nonylopyranosylonic acid The following compound was synthesized analogously to Compound A, using 11 instead of 5.
Yield 22.4 mg (73%).
¹H NMR (400 MHZ, MeOD) δ 0.90 (m), 1.30-1.40 (m), 1.47-1.63 (m), 2.01 (s, 3H), 2.18-2.26 (m), 2.45 (t, 2H), 2.81-2.85 (m, 1H), 3.17 (t, 2H), 3.36 (t, 2H), 4.45-3.88 (m).
HRMS calcd. for $C_{50}H_{87}N_3O_{14}$ (M+Na)⁺ 976.6086, found 976.5989.

Compound H 6,25-diaza-10,13,16,19,22-pentaoxa-7,26-dioxo-35,37-pentakontadiynyl 5-acetamido-3,5-dideoxy-D-glycero-α-D-galacto-2-nonylopyranosylonic acid The following compound was synthesized analogously to Compound A, using 12 instead of 5.
Yield 16.6 mg (84%).
¹H NMR (400 MHZ, MeOD) δ 0.90 (t, 3H), 1.27-1.40 (m), 1.47-1.63 (m), 2.01 (s, 3H), 2.12-2.26 (m), 2.45-2.48 (m, 2H), 2.81-2.85 (m, 1H), 3.10-3.23 (m, 2H), 3.35-3.38 (m, 2H), 3.45-3.88 (m).
HRMS calcd. for $C_{54}H_{95}N_3O_{16}$ (M+Na)⁺ 1064.6610, found 1064.6732.

Compound I 6,46-diaza-10,13,16,19,22,25,28,31,34,37,40,43,46-dodekaoxa-7,47-dioxo-56,58-henheptakonta-diynyl 5-acetamido-3,5-dideoxy-D-glycero-α-D-galacto-2-nonylopyranosylonic acid The following compound was synthesized analogously to Compound A, using 13 instead of 5.
Yield 17.2 mg (98%).
¹H NMR (400 MHZ, MeOD) δ 0.90 (t, 3H), 1.30-1.40 (m), 1.49-1.63 (m), 2.01 (s, 3H), 2.18-2.26 (m), 2.46 (t, 2H), 2.81-2.85 (m, 1H), 3.18 (t, 2H), 3.35-3.38 (m, 2H), 3.45-3.88 (m)

HRMS calcd. for $C_{68}H_{123}N_3O_{23}$ $(M+Na)^+$ 1372.8445, found 1372.8213.

Compound J 6-aza-7-oxo-16,18-hentriakonta-diynyl 5-acetamido-3,5-dideoxy-D-glycero-α-D-galacto-2-nonylopyranosylonic acid The following compound was synthesized analogously to Compound A, using 14 instead of 5.
Yield 24.2 mg (63%).
$^1$H NMR (400 MHZ, MeOD) δ 0.90 (t, 3H), 1.30-1.41 (m), 1.47-1.62 (m), 2.03 (s, 3H), 2.18 (t), 2.24 (t), 2.80-2.84 (m, 1H), 3.14-3.18 (m, 2H), 3.45-3.90 (m).
HRMS calcd. for $C_{41}H_{70}N_2O_{10}$ $(M+H)^+$ 751.5103, found 751.4911.

Compound K 6-aza-7-oxo-16,18-dokosanyl 5-acetamido-3,5-dideoxy-D-glycero-α-D-galacto-2-nonylopyranosylonic acid The following compound was synthesized analogously to Compound A, using 15 instead of 5.
Yield 29 mg (quantitative %).
$^1$H NMR (400 MHZ, MeOD) δ 0.90 (t, 3H), 1.25-1.41 (m), 1.46-1.63 (m), 1.85-1.95 (m), 2.02 (s, 3H), 2.17 (t, 2H), 2.83 (dd, 1H), 3.15 (t, 2H), 3.45-3.90 (m).

Formation of Aggregates and their Subsequent Formulation in Aqueous Solution

Formulations were carried out by either a probe type sonicator (50% output, microtip) or an extrusion device manufactured by Northern Lipids (Vancouver, BC, Canada) using polycarbonate membrane filters, pore-size 100 nm or 200 nm;
DCM Dichloromethane
DPPC Dipalmitoylphosphatidylcholine
MCT medium chain triglyceride
s-PC soy-phosphatidylcholine
$T_m$ melting temperature Formulation 13 (Control without any Sialic Acid Residues)

10,12-pentacosadiynoic acid (3.7 mg, 10 μmol) was mixed in DCM and put in a glass vial. The solvent was evaporated and distilled water (10 mL) was added. The mixture was probe sonicated until a clear solution was obtained, approximately 15 minutes. The warm solution was filtered through a nylon filter (0.8 μm) to remove any undispersed lipid and traces of titanium particles from the probe.

Formulation 14H

The formulation was performed in an analogous method to Formulation 13, using compound H (0.1 mg, 0.1 μmol) and 10,12-pentacosadiynoic acid (3.7 mg, 9.9 μmol).

Formulation 15H

The formulation was performed in an analogous method to Formulation 13, using compound H (0.5 mg, 0.5 μmol) and 10,12-pentacosadiynoic acid (3.6 mg, 9.5 μmol).

Formulation 16H

The formulation was performed in an analogous method to Formulation 13, using compound H (1.0 mg, 1.0 μmol) and 10,12-pentacosadiynoic acid (3.4 mg, 9.0 μmol).

Formulation 20J

The formulation was performed in an analogous method to Formulation 13, using compound J (0.75 mg, 1.0 μmol) and 10,12-pentacosadiynoic acid (3.4 mg, 9.0 μmol).

Formulation 24H

The formulation was performed in an analogous method to Formulation 13, using compound H (1.0 mg, 1.0 μmol), DPPC (3.3 mg, 4.5 μmol) and cholesterol (1.7 mg, 4.5 μmol).

Formulation 41H

Compound H (2.1 mg, 2.0 μmol) and 10,12-pentacosadiynoic acid (3.0 mg, 8.0 μmol) were mixed in $CHCl_3$ and put in a glass vial. The mixture was vortexed and the solvent was evaporated with nitrogen to yield a thin film of the lipids on the glass. Milli-Q water (10 mL) was added and the mixture was hydrated at 65° C. under stirring over night. The liposomal dispersion was then sequentially (10 cycles) passed through a polycarbonate membrane filter (200 nm pore-size) above the $T_m$ (65° C.) by an extrusion device.

Formulation 42D

The formulation was performed in an analogous method to Formulation 41H, using compound D (1.0 mg, 1.0 μmol) and 10,12-pentacosadiynoic acid (3.4 mg, 9.0 μmol). The extrusion was performed by a polycarbonate membrane filter (pore-size 100 nm).

Formulation 44F

The formulation was performed in an analogous method to Formulation 41H, using compound F (1.3 mg, 1.0 μmol) and 10,12-pentacosadiynoic acid (3.4 mg, 9.0 μmol). The extrusion was performed by a polycarbonate membrane filter (pore-size 100 nm).

Formulation 47E

The formulation was performed in an analogous method to Formulation 41H, using compound E (1.0 mg, 1.0 μmol) and 10,12-pentacosadiynoic acid (3.4 mg, 9.0 μmol). The extrusion was performed by a polycarbonate membrane filter (pore-size 100 nm).

Formulation 48B

The formulation was performed in an analogous method to Formulation 41H, using compound B (1.0 mg, 1.0 μmol) and 10,12-pentacosadiynoic acid (3.4 mg, 9.0 μmol). The extrusion was performed by a polycarbonate membrane filter (pore-size 100 nm).

Formulation 49G

The formulation was performed in an analogous method to Formulation 41H, using compound G (1.0 mg, 1.0 μmol) and 10,12-pentacosadiynoic acid (3.4 mg, 9.0 μmol). The extrusion was performed by a polycarbonate membrane filter (pore-size 100 nm).

Formulation 50I

The formulation was performed in an analogous method to Formulation 41H, using compound I (1.4 mg, 1.0 μmol) and 10,12-pentacosadiynoic acid (3.4 mg, 9.0 μmol). The extrusion was performed by a polycarbonate membrane filter (pore-size 100 nm).

Formulation 56H

The formulation was performed in an analogous method to Formulation 41H, using compound H (1.0 mg, 1.0 μmol), s-PC/MCT (1.0 mg/3.4 mg). The extrusion was performed, after probe sonication for 2 minutes, by a polycarbonate membrane filter (pore-size 100 nm).

Formulation 59H

The formulation was performed in an analogous method to Formulation 41H, using compound H (1.0 mg, 1.0 μmol), s-PC (7.2 mg, ~9 μmol). The extrusion was performed by a polycarbonate membrane filter (pore-size 100 nm).

Formulation Example 1

Compound H and PDA were dissolved in chloroform at a concentration of 10.1 mg/mL and 3.41 mg/mL, respectively. The resulting solutions were stored in a refrigerator. To a 10 mL round-bottomed flask were added 100 μL of the Compound A solution and 1 mL of the PDA solution. The mixture was evaporated to dryness at 35° C. on a rotavapor (Heidolph Laborota 4001, Germany). To the resulting dry film was added 10 mL of membrane-filtered water (Milli-Q). The flask was put in a sonication bath (Bandelin Sonora Digitech, Germany) and sonicated for 10 min at 50° C. and for 5 min at about 70° C. This resulted in an opaque, homogeneous dispersion with a slightly pink colour.

Formulation Example 2

The dispersion from Formulation Example 1 was heated to about 80° C. in a water bath and extruded 11 times through a polycarbonate membrane with a pore size of 100 nm (Avestin LiposoFast, Canada). The resulting fine dispersion was transferred to a quarts cuvette and illuminated with UV light for 5 min at room temperature (ICT Beam Boost Photoreactor, Germany). This gave a dark blue coloured dispersion.

Formulation Example 3

A dry lipid film was prepared as described in Formulation Example 1. To the film was added 10 mL of an aqueous solution consisting of 2.6% (w/w) of glycerol and 0.50% (w/w) of Hypromellose (Sigma-Aldrich, H-3785). After hydration for 15 min at about 45° C. in a sonication bath, a slightly viscous preparation was obtained, which is suitable for instilling into the eye.

Biological Testing

The biological activity of compounds, aggregates and formulation disclosed herein where evaluated in various assays which are disclosed below.

Cells

HCE (human corneal epithelial) and A549 cells were grown as previously described (Araki-Sasaki, K., Ohasi, K. Y., Sasabe, T., Hayashi, K., Watanabe, H., Tano, Y., Handa, H., 1995. "An SV-40-immortalized human corneal epithelial cell line and its characterization." Invest. Ophtahlmol. 36, 614-621 and Amberg, N., Edlund, K., Kidd, A. H., Wadell, G., 2000a. Adenovirus type 37 uses sialic acid as a cellular receptor. J. Virol. 74, 42-48.).

Viruses

HAdV37 (strain 1477) virions were produced as follows: 0.3 mL of HAdV37 inoculation material (prepared from infected A549 cells) was added to A549 cells (175 cm² flasks) and incubated for 2 h at 37° C. Non-internalized viruses were removed by washing, and the cells were further incubated at 37° C. in Dulbecco's modified Eagle's Medium (DMEM; Sigma-Aldrich) supplemented with 1% fetal calf serum (FCS; Sigma-Aldrich). About 72 h later, the cells were pelleted, resuspended in Tris-HCl, pH 7.4, and freeze-thawed three times. After another round of centrifugation, the supernatant was loaded onto a discontinuous CsCl gradient (densities: 1.27 g/mL, 1.32 g/mL, and 1.37 g/mL, in 20 mM Tris-HCl, pH 8.0; Sigma-Aldrich) and centrifuged at 25,000 rpm (SW41 rotor, Beckman Optima L-80 XP ultracentrifuge; Beckman Coulter Inc.) for 2.5 h at +4° C. The virion band was harvested and desalted on a NAP column (Amersham Biosciences AB, Uppsala, Sweden) in sterile PBS buffer supplemented with 10% glycerol (Sigma-Aldrich). Aliquoted virions were then stored at −80° C. until further use. $^{35}$S-labeled Ad37 virions were produced as above with the following exceptions: 20 h post infection the cells were starved for 2 h in methionine-cysteine-free DMEM (Sigma-Aldrich). Thereafter isotope (1.4 mCi/flask; NEG-772 Easytag express protein labeling mix; Perkin-Elmer) was added. L-cysteine (final concentration 2 mM; Sigma-Aldrich;) was added 23 h and 48 h post-infection and 1-methionine (final concentration 1 mM; Sigma-Aldrich) was added 37.5 h and 48 h post-infection. The specific radioactivity of labeled virions was determined to be $4 \times 10^{-6}$ cpm per virion. The identity of HAdV-37 was determined by digesting viral DNA with restriction enzymes and compared to established patterns for HAdV-37 prototype strain (Wadell, G., Sundell, G., de Jong, J. C., 1981. Characterization of candidate adenovirus 37 by SDS-polyacrylamide gel electrophoresis of virion polypeptides and DNA restriction site mapping. J. Med. Virol. 7, 119-125.).

Antibodies

Rabbit polyclonal anti-HAdV-37 serum was prepared as described previously (Wadell, G., Allard, A., Hierholzer, J. C., 1999. Adenoviruses. In: Murray, P. R., Baron, E. J., Pfaller, M. A., Tenover, F. C., Yolken, R. H. (Eds.), Manual of Clinical Microbiology, 7th ed. ASM Press, Washington, pp. 970-982.).

Binding Assay

Adherent HCE cells were detached with PBS containing 0.05% EDTA (PBS-EDTA; Merck, Darmstadt, Germany) and recovered in growth medium for one hour at 37° C. After washing, $2 \times 10^5$ HCE cells were prepelleted in V-shaped 96 well microplates, then resuspended and incubated with $10^4$ 35S-labeled HAdV-37 virions/cell supplemented with different concentrations of the tested compounds in 50 μL binding buffer (BB: DMEM containing 1% bovine serum albumin [Roche AB, Stockholm, Sweden], penicillin/streptomycin [Gibco, Carlsbad, Calif., USA] and HEPES [EuroClone, Milano, Italy]), pH 7.4, at 4° C. with gentle agitation.

Prior to the addition to the cells, the HAdV-37 virions were thus pretreated with various concentrations of the aggregate to be tested in 96-well plates 1 h at 4° C. with gentle agitation.

After one additional hour, unbound virions were removed by washing, and the cell-associated radioactivity was measured with a Wallac 1409 scintillation counter (Perkin-Elmer).

By comparing the cell-associated radioactivity for cells treated with different concentrations of the tested aggregate, the $IC_{50}$ could be determined.

In Table 1 below, test results for some of formulations disclosed herein are given.

TABLE 1 inhibition of the binding of HAdV-37 virions to HCE cells by formulations disclosed herein

| Formulation | IC50 |
| --- | --- |
| 13 (control) | − |
| 14H | +++ |
| 15H | +++ |
| 16H | ++++ |
| 20J | ++/+++ |
| 24H | + |
| 41H | ++ |
| 42D | +++ |
| 44F | +++ |
| 47E | +++ |
| 48B | + |
| 49G | + |
| 50I | +++ |
| 56H | + |

− No inhibition
+ more than 0% but less than 50% inhibition at 50 to 100 μM
++ 50% inhibition at 25 to 50 μM
+++ 50% inhibition at 5 to 25 μM
++++ 50% inhibition at 5 μM or less As seen from Table 1, various compounds and aggregates disclosed herein are able to inhibit the binding of HAdV-37 virions to HCE cells. In this context it should be noted that the $IC_{50}$ of sialic acid is about 2-5 mM. Furthermore, it should be noted that $IC_{50}$, when referring to formulations, refers to the concentration of sialic acid residues in the formulation.

Aggregation Assay $^{35}$S-labeled HAdV37 virions ($5 \times 10^8$ per well) were incubated with or without Formulation 16H (containing 0.05 mM sialic acid residues) in BB at +4° C. One hour later, the samples were centrifuged at different speeds (1000 rpm, 4000 rpm, 7000 rpm, 10,000 rpm, 13,000 rpm) using a Beckman Coulter Microfuge 22R Centrifuge (Beckman Coulter Inc., Fullerton, Calif., USA). The radioactivity in the supernatant (top 90 μL) and in the pellet (lower 10 μL) was measured using a liquid scintillation counter as described above.

As seen from FIG. 1, Formulation 16H causes aggregation of HAdV37. S denotes supernatant and P denotes pellet. Accordingly, compound H is a multivalent specie with regard to its sialic acid residues.

Infectivity Assay

Non-labeled HAdV-37 virions ($4 \times 10^8$ per well in 3004 BB) were incubated at +4° C. in 24-well plates together with different concentrations of Formulation 16H. After 1 h, the mixtures were added to HCE cells grown as monolayers on glass slides in 24-well plates ($2 \times 10^5$ cells/well) and incubated on ice. One hour later, the wells were washed three times with +4 $C_1$% SHEM (supplemented hormone epithelial medium (Araki-Sasaki, K., Ohasi, K. Y., Sasabe, T., Hayashi, K., Watanabe, H., Tano, Y., Handa, H., "An SV-40-immortalized human corneal epithelial cell line and its characterization" Invest. Ophtahlmol. 1995, 36, 614-621)) in order to remove unbound virions, and incubated for 44 h at 37° C. to allow infection. The glass slides were rinsed with phosphate-buffered saline (PBS pH 7.4), fixed with methanol (99%) and incubated with a rabbit polyclonal anti-HAdV37 serum (diluted 1:200 in PBS) at RT. One hour later, the slides were washed three times in PBS and incubated with swine anti-rabbit FITC-labeled antibody (DakoCytomation, Glostrup, Denmark) in RT (diluted 1:200 in PBS). The slides were mounted with fluorescent mounting medium (DakoCytomation) and examined in an immunofluorescence microscope (Axioskop2, Carl Zeiss, Germany; 10× magnification).

Figure 2:
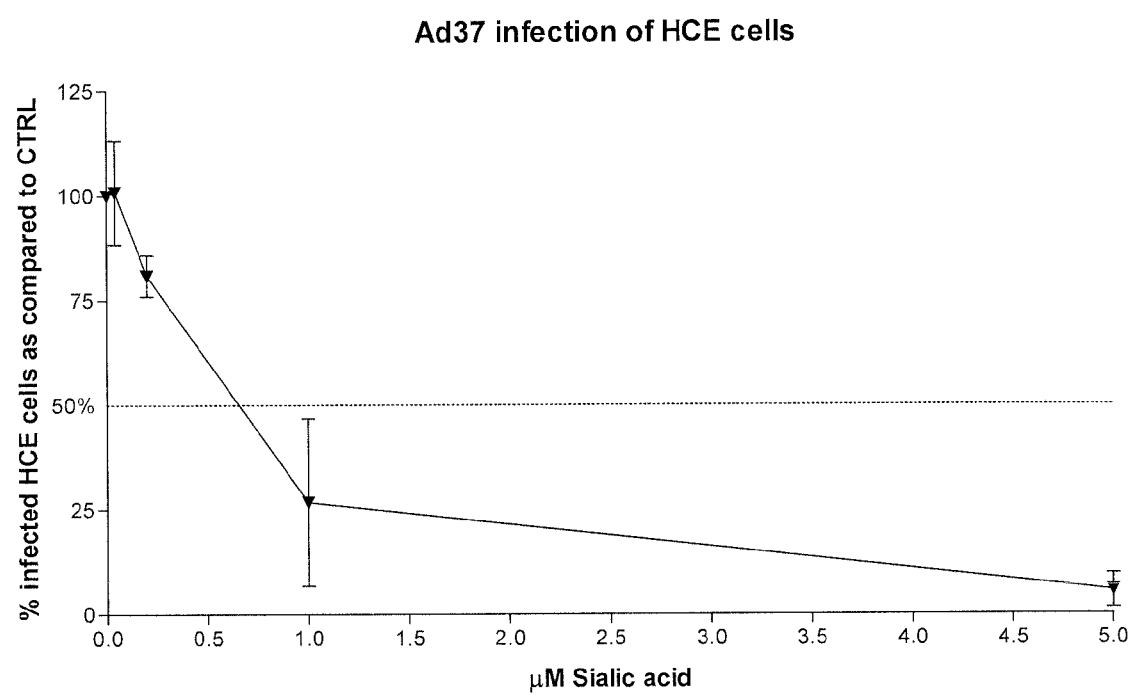
FIGS. 2 and 3 depict the ability of aggregates according to the present invention to inhibit HAdV37 to infect HCE cells at various concentrations.
Figure 3:
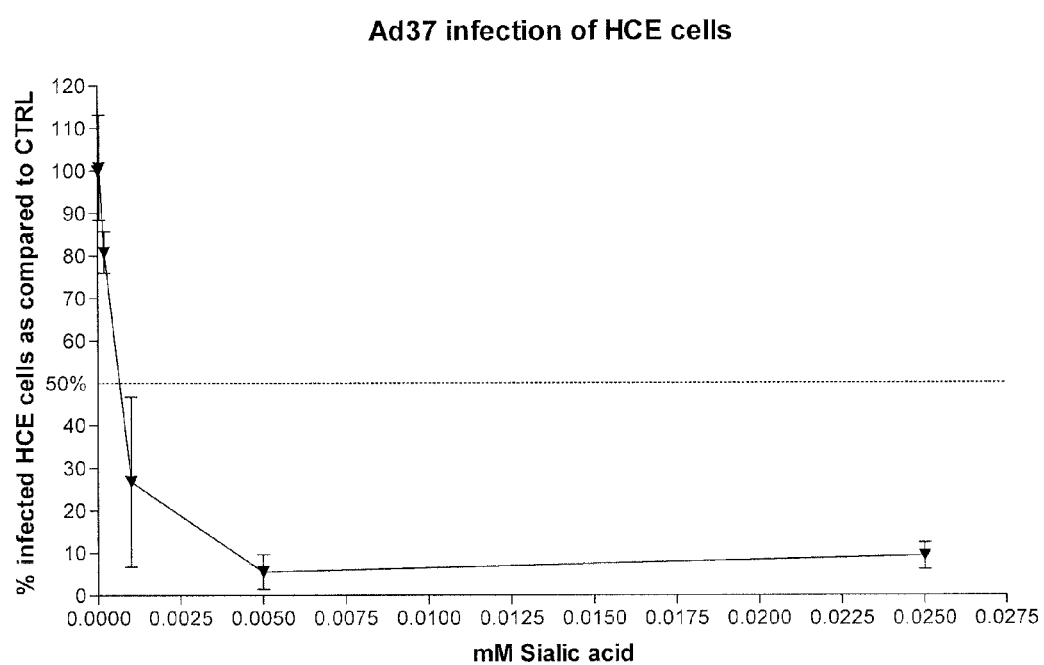

As seen from FIGS. 2 and 3, Formulation 16H significantly inhibits HAdV-37 from infecting HCE cells ($IC_{50}$ is approx. 0.7 μM with respect to the sialic acid residues present in the aggregates).

The invention claimed is:

1. A compound according to formula (I)

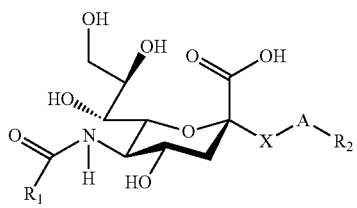

(I)

wherein
R1 is a methyl or ethyl group;
R2 is R3, R4 or R8;
"X" is O, S, or NH; and
"A" is a C3-7 alkanediyl if R2 is R3 and a C2-7 alkanediyl if R2 is R4 or R8, wherein X and R2 are connected to different carbon atoms of said alkanediyl and wherein said different carbon atoms are the carbon atoms in said alkanediyl being most spaced apart;
R3 is selected from the group consisting of N(C0-3 alkyl)C(O)R5, OC(O)R5, C(O)N(C0-3 alkyl)R5 and C(O)OR5, wherein R5 is a straight carbon chain comprising 14 to 30 carbon atoms;
said carbon chain is saturated or comprises one or more double and/or triple bond(s);
furthermore, said carbon chain is unsubstituted or substituted with one or more C1-C5 alkyl groups;
R4 is a substituent according to formula (II)

$$D(CH_2)_m(OCH_2CH_2)_n(CH_2)_pER_7 \quad (II)$$

wherein
"D" is connected to "A";
"D" is selected from the group consisting of N(C0-3 alkyl)C(O), OC(O), C(O)N(C0-3 alkyl), and C(O)O;
the integer "m" is 0 (zero) to 3;
the integer "n" is 1 to 15;
the integer "p" is 0 (zero) to 3;
"E" is selected from the group consisting of N(C0-3 alkyl)C(O), OC(O), C(O)N(C0-3 alkyl), and C(O)O;
R7 is selected from the group consisting of R5, as defined above, and R6, wherein R6 is a substituent according to formula (III)

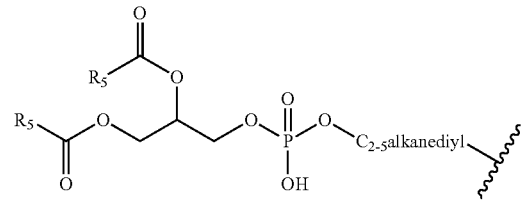

(III)

wherein each R5, independently, is as defined above, and the C2-5 alkanediyl is attached to "E"; and
R8 is selected from the group consisting of N(C0-3 alkyl)C(O)R9, OC(O)R9, C(O)N(C0-3 alkyl)R9 and C(O)OR9, wherein R9 is a substituent according to formula (IV)

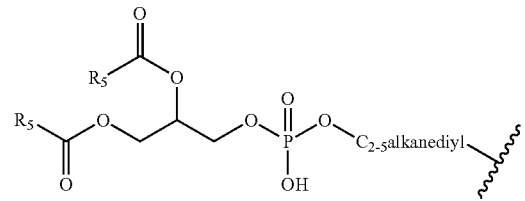

(IV)

wherein each R5, independently, is as defined above;
as an acid in its non-charged protonated form, a pharmaceutically acceptable addition salt, solvate, or solvate of a salt thereof.

2. A compound according to claim 1, wherein "A" is a non-branched straight chain C2-5 alkanediyl; R1 is methyl; "X" is O; R2 is R4 or R8; and R5 is a unsubstituted straight carbon chain.

3. A compound according to claim 2, wherein R2 is R4; and R7 is R5, wherein R5 is an unsubstituted straight carbon chain comprising 20 to 30 carbon atoms.

4. A compound according to claim 3, wherein R5 comprises at least one double or triple bond.

5. The compound according to claim 4, wherein R5 comprises two conjugated triple bonds.

6. A compound according to claim 1, wherein R2 is R4; R7 is R5; the integer "n" is 4 to 15; D is NHC(O) or OC(O); the integer "m" is 2; the integer "p" is 0 (zero); and E is NHC(O) or OC(O); or wherein R2 is R4; R7 is R5; the integer "n" is 4 to 15; D is C(O)NH or C(O)O; the integer "m" is 2; the integer "p" is 0 (zero); and E is NHC(O) or OC(O).

7. A compound according to claim 1, wherein R2 is R3; and R3 is NHC(O)R5.

8. A compound according to claim 1, wherein said compound is selected from the group consisting of 6,19-diaza-10,13,16-trioxa-7,20-dioxo-tritetrakontanyl 5-acetamido-3,5-dideoxy-D-glycero-α-D-galacto-2-nonylopyranosylonic acid, 6,25-diaza-10,13,16,19,22-pentaoxa-7,26-dioxo-nonatetrakontanyl 5-acetamido-3,5-dideoxy-D-glycero-α-D-galacto-2-nonylopyranosylonic acid 6,46-diaza-10,13,16,19,22,25,28,31,34,37,40,43,46-dodekaoxa-7,47-dioxo-tetrahexakontanyl 5-acetamido-3,5-dideoxy-D-glycero-α-D-galacto-2-nonylopyranosylonic acid, 6,19-diaza-10,13,16-trioxa-7,20-dioxo-29,31-tetratetrakonta-diynyl 5-acetamido-3,5-dideoxy-D-glycero-α-D-galacto-2-nonylopyranosylonic acid 6,25-diaza-10,13,16,19,22-pentaoxa-7,26-dioxo-35,37-pentakontadiynyl 5-acetamido-3,5-dideoxy-D-glycero-α-D-galacto-2-nonylopyranosylonic acid and 6,46-diaza-10,13,16,19,22,25,28,31,34,37,40,43,46-dodekaoxa-7,47-dioxo-56,58-henheptakonta-diynyl 5-acetamido-3,5-dideoxy-D-glycero-α-D-galacto-2-nonylopyranosylonic acid. A compound according to formula (I) may be selected from the group consisting of 6,19-diaza-10,13,16-trioxa-7,20-dioxo-29,31-tetratetrakonta-diynyl 5-acetamido-3,5-dideoxy-D-glycero-α-D-galacto-2-nonylopyranosylonic acid, 6,25-diaza-10,13,16,19,22-pentaoxa-7,26-dioxo-35,37-pentakontadiynyl 5-acetamido-3,5-dideoxy-D-glycero-α-D-galacto-2-nonylopyranosylonic acid and 6,46-diaza-10,13,16,19,22,25,28,31,34,37,40,43,46-dodekaoxa-7,47-dioxo-56,58-henheptakonta-diynyl 5-acetamido-3,5-dideoxy-D-glycero-α-D-galacto-2-nonylopyranosylonic acid.

9. A compound according to claim 1, wherein said compound is present as a pure stereoisomer or in an anomeric mixture comprising said compound, in which anomeric mixture the α-anomer prevails.

10. An aggregate comprising a plurality of the compound according to claim 1 and a plurality of an amphiphilic molecule separate from said compound and capable of forming bilayers in water, wherein said amphiphilic molecule comprises a linear carbon chain comprising at least 12 carbon atoms; and optionally at least on triple bond, and/or a carboxy group.

11. The aggregate according to claim 10, wherein the aggregate comprises 0.1 to 25 mol % of said compound, and at least 40 mol % of said amphiphilic molecule.

12. The aggregate according to claim 10, wherein said amphiphilic molecule is 10,12-pentacosadiynoic acid.

13. A pharmaceutical composition comprising an aggregate according to claim 10 and at least one pharmaceutical acceptable excipient, wherein said composition is an aqueous composition, and wherein said composition comprises 0.001 to 10 mM.

14. The pharmaceutical composition according to claim 13, wherein said aqueous composition has a water content of at least 90 wt %.

15. The pharmaceutical composition according to claim 13, wherein said composition comprises an agent, to provide an isotonic solution, a thickening agent, an additional antiviral compound, and/or a local anesthetic.

16. The pharmaceutical composition according to claim 15, wherein said composition is for administration to the eye.

17. A method for mitigation and/or treatment of an ocular infection caused by a virus, which virus binds to terminal sialic residues present on the cell surface of the cell to be infected by said virus, said method comprising administering to a mammal, in need of such mitigation and/or treatment, a therapeutically effective amount compound according to claim 1.

18. The method according to claim 17, wherein said compound is administered to the eye.

19. The method according to claim 17, wherein said ocular infection caused by a virus is epidemic keratoconjunctivitis.

20. The method according to claim 17, wherein said virus is selected from the group consisting of HAdV-8, HAdV-19, HAdV-37, HAdV-53, HAdV-54, and HAdV-22, 37/H8.

* * * * *